(12) United States Patent
Kugimoto et al.

(10) Patent No.: US 8,962,826 B2
(45) Date of Patent: Feb. 24, 2015

(54) METHOD FOR PRODUCING AMIDE COMPOUND

(71) Applicant: Ube Industries, Ltd., Ube-shi (JP)

(72) Inventors: Junichi Kugimoto, Ube (JP); Joji Kawai, Ube (JP); Kazuo Yamato, Ube (JP); Masahide Okada, Ube (JP); Tsunemi Sugimoto, Ube (JP); Hiroshi Matsumoto, Ube (JP)

(73) Assignee: Ube Industries, Ltd., Ube-shi (JP)

( * ) Notice: Subject to any disclaimer, the term of this patent is extended or adjusted under 35 U.S.C. 154(b) by 0 days.

(21) Appl. No.: 14/141,916

(22) Filed: Dec. 27, 2013

(65) Prior Publication Data

US 2014/0114062 A1    Apr. 24, 2014

Related U.S. Application Data

(62) Division of application No. 13/635,092, filed as application No. PCT/JP2011/056098 on Mar. 15, 2011.

(30) Foreign Application Priority Data

| Mar. 15, 2010 | (JP) | 2010-057123 |
|---|---|---|
| Mar. 31, 2010 | (JP) | 2010-080851 |
| Jul. 30, 2010 | (JP) | 2010-172322 |
| Nov. 10, 2010 | (JP) | 2010-252108 |

(51) Int. Cl.
C07D 225/02    (2006.01)
C07D 201/04    (2006.01)
C07D 201/06    (2006.01)

(52) U.S. Cl.
CPC ............ *C07D 201/06* (2013.01); *C07D 201/04* (2013.01); *C07D 225/02* (2013.01)
USPC ......................................... 540/464; 540/535

(58) Field of Classification Search
USPC ................................................ 540/464, 535
See application file for complete search history.

(56) References Cited

U.S. PATENT DOCUMENTS

| 3,825,532 | A | 7/1974 | Kern et al. |
|---|---|---|---|
| 5,362,870 | A | 11/1994 | Higashio et al. |
| 5,496,941 | A | 3/1996 | Ritz et al. |
| 5,539,106 | A | 7/1996 | Thijert et al. |
| 6,252,058 | B1 | 6/2001 | Thompson |
| 2003/0139596 | A1 | 7/2003 | Kuroda et al. |
| 2006/0281952 | A1 | 12/2006 | Teles et al. |
| 2009/0326276 | A1 | 12/2009 | Teles et al. |
| 2010/0029931 | A1 | 2/2010 | Shibamoto et al. |
| 2010/0029932 | A1 | 2/2010 | Ishii et al. |
| 2010/0267944 | A1 | 10/2010 | Kugimoto et al. |
| 2010/0324283 | A1 | 12/2010 | Ishihara et al. |
| 2011/0092699 | A1 | 4/2011 | Iwahama et al. |

FOREIGN PATENT DOCUMENTS

| DE | 1 004 616 B | 3/1957 |
|---|---|---|
| DE | 10 81 884 B | 5/1960 |
| DE | 1 253 716 B | 11/1967 |
| DE | 75 083 A | 8/1970 |
| EP | 0 570 110 A1 | 11/1993 |
| EP | 0 635 487 A1 | 1/1995 |
| EP | 1 329 448 A1 | 7/2003 |
| EP | 2 123 635 A1 | 11/2009 |
| EP | 2 223 911 A1 | 9/2010 |
| GB | 969993 A | 9/1964 |
| GB | 1 467 565 | 3/1977 |
| JP | A-S51-41376 | 4/1976 |
| JP | B-S52-12198 | 4/1977 |
| JP | A-H05-310706 | 11/1993 |
| JP | A-H07-53510 | 2/1995 |
| JP | A-2002-12585 | 1/2002 |
| JP | A-2004-99585 | 4/2004 |
| JP | A-2006-219470 | 8/2006 |
| JP | A-2006-528649 | 12/2006 |
| JP | A-2007-506695 | 3/2007 |
| JP | A-2008-156277 | 7/2008 |
| JP | A-2008-162935 | 7/2008 |
| JP | A-2009-298706 | 12/2009 |
| WO | WO 2005/014538 A1 | 2/2005 |
| WO | WO 2007/125002 | 11/2007 |
| WO | WO 2008/096873 A1 | 8/2008 |
| WO | WO 2009/069522 A1 | 6/2009 |

OTHER PUBLICATIONS

International Preliminary Report on Patentability issued in International Application No. PCT/JP2011/056098 on Nov. 1, 2012.
Extended Search Report issued in European Patent Application No. 11756317.1 on Aug. 2, 2013.
Cesare et al., "A High-Yielding General Synthesis of α-Lactams," Synthesis, No. 12, pp. 1716-1720, 2002.
Kobayashi et al., "$Ph_3P$-$(PyS)_2$-$CH_3CN$ as an Excellent Condensing System for β-Lactam Formation from β-Amino Acids," J. Am. Chem. Soc., No. 103, pp. 2406-2408, 1981.
Oya et al., "Crystals of Binary Molecular Compounds Formed by Hydrogen Bonds," Journal of Structural Chemistry, No. 15, pp. 578-583, 1974.
Office Action issued on Jun. 27, 2013 in Chinese Patent Application No. 201180024285.7.
Extended European Search Report issued in European Patent Application No. 14156597.8 on Aug. 5, 2014.
Taber et al., "The Synthesis of Laurolactam from Cylocodecanone Via a Beckmann Rearrangement," J. Chem. Educ. 2010, vol. 87., No. 12, p. 1392, published online Sep. 15, 2010.
Taber et al., The Synthesis of Laurolactam from Cyclododecanone Via a Beckmann Rearrangement , (supporting lab documentation for document 4), pp. 1-16, published online Sep. 15, 2010.

*Primary Examiner* — Bruck Kifle
(74) *Attorney, Agent, or Firm* — Knobbe Martens Olson & Bear LLP

(57)    ABSTRACT

A method for producing a high purity, high quality amide compound, particularly a lactam. An amount of each of a halide, an aldehyde compound, an alcohol compound and a nitrile compound contained in a solution recycled into an oxime-forming step is controlled to an amount of 0.4 mol % or less based on the ketone as a starting material. One or more of a ketone, an oxime and an amide compound are purified by hydrogenation and/or crystallization for eliminating impurities containing a double bond. A content of impurities having a cyclic bridge structure is controlled using a cycloalkanone purified by recrystallization.

5 Claims, No Drawings

METHOD FOR PRODUCING AMIDE COMPOUND

RELATED APPLICATIONS

This application is a divisional of U.S. patent application Ser. No. 13/635,092, filed Sep. 14, 2012, which is the U.S. National Phase of PCT/JP2011/056098, filed Mar. 15, 2011, designating the U.S., and published in Japanese as WO2011/115132 on Sep. 22, 2011, which claims priority to Japanese Patent Application No. 2010-057123, filed Mar. 15, 2010; Japanese Patent Application No. 2010-080851, filed Mar. 31, 2010; Japanese Patent Application No. 2010-172322, filed Jul. 30, 2010; and Japanese Patent Application No. 2010-252108, filed Nov. 10, 2010, the entire contents of which are incorporated herein by reference in their entireties

TECHNICAL FIELD

The present invention relates to a process for manufacturing an amide compound, for example, a lactam, useful as a starting material for medical drugs, agricultural chemicals, dyes and polyamides.

BACKGROUND ART

A common industrial process for producing an amide compound comprises producing an oxime compound from a corresponding ketone and hydroxylamine followed by Beckmann rearrangement of the oxime compound. For example, ε-caprolactam, which is industrially useful, is produced by Beckmann rearrangement of cyclohexanone oxime. The rearrangement is generally conducted using concentrated sulfuric acid and oleum, and since these strong acids must be used in the stoichiometric amounts or more, salts such as ammonium sulfate are formed as byproducts during neutralization in a far larger amount than that of the product ε-caprolactam. In other words, the process requires many facilities and large amounts of starting materials and energy for producing a large amount of auxiliary materials such as sulfuric acid and treating byproducts such as sodium sulfate.

In contrast, a liquid-phase Beckmann rearrangement reaction using a catalyst requires no auxiliary materials and produces less byproducts, and is, therefore, expected to be put to practical use. A Beckmann rearrangement catalyst in a liquid phase has been extensively studied. For example, an aromatic-ring-containing compound disclosed in Patent Reference No. 1 can be used, which (i) contains, as an aromatic-ring member, at least one carbon atom having a leaving group and (ii) contains at least three aromatic-ring members which are either or both of heteroatoms or/and carbon atoms having an electron-withdrawing group, and (iii) wherein, two of the heteroatoms and/or carbon atoms having an electron-withdrawing group are at the ortho- or para-position to the carbon atom having a leaving group. Examples of a practically used Beckmann rearrangement catalyst include trichlorotriazine (also known as cyanuric chloride, 2,4,6-trichloro-1,3,5-triazine, abbreviated as "TCT") and hexachlorophosphazene (Patent Reference No. 13).

Patent Reference No. 2 has described that a Beckmann rearrangement reaction is conducted in a nonpolar solvent using a catalyst disclosed in Patent Reference No. 1. Patent Reference Nos. 3 and 4 have described a process of Beckmann rearrangement of an oxime compound using an analogous compound to a catalyst disclosed in Patent Reference No. 1. Patent Reference Nos. 5 and 6 have disclosed Beckmann rearrangement of an oxime compound using an acid chloride such as thionyl chloride as a catalyst.

Patent Reference Nos. 7 and 8 have disclosed a specific process for producing an amide compound by Beckmann rearrangement using a catalyst disclosed in Patent Reference No. 1, but have not specifically described recycling of a solvent and the like.

Lactams are mainly used for polymers or copolymers for yarns, fibers, films and the like, and in some cases must have purity satisfying strict standard values.

Examples of typical standard values include those based on an absorbance such as a light transmittance difference (LT. diff, detailed later), a UV value (a UV absorbance (at a wavelength 290 nm) of a 50% by weight aqueous solution of a lactam is measured within a cell having a width of 1 cm), and a PAN value (ISO standard 8660).

As a method for improving a UV value and a PAN value among these standard values, many techniques have been disclosed, including distillation, solvent washing, crystallization/recrystallization, acid treatment, alkali treatment, oxidation, hydrogenation and the like of a lactam product. For example, Patent Reference No. 14 has described that a PAN value can be improved by preventing a nickel catalyst from entering a reboiler in hydrogenating a caprolactam over a nickel catalyst followed by purification by distillation.

Patent Reference No. 15 has disclosed influence of impurities in cyclododecanone as a starting material on an LT. diff of laurolactam that is a desired compound.

A known method for achieving a low UV value is hydrogenation of a lactam in the presence of a catalyst. For example, Patent Reference No. 9 has disclosed a method for hydrogenating a caprolactam prepared by a Beckmann rearrangement reaction, in the presence of a suspended hydrogenation catalyst. Furthermore, Patent Reference Nos. 10 and 11 have disclosed a method for hydrogenating a caprolactam after treatment with activated charcoal and an ion-exchange resin. Patent Reference No. 12 has disclosed a method for hydrogenating a lactam prepared by cyclization hydrolysis of an aminonitrile, in the presence of a hydrogenation catalyst.

The above techniques relate to improvement in the standard values of a lactam prepared by Beckmann rearrangement of an oxime using a strong acid such as sulfuric acid. There have disclosed no purification methods for improving the above standard values for a lactam prepared by a production process without a large amount of ammonium sulfate as a byproduct of a Beckmann rearrangement reaction being produced. Furthermore, the above disclosed techniques show relationship between a treatment method and UV value, PAN value or the like, but do not identify substances causing deterioration in standard values or not show relationship between the concentrations of the causative substances and the standard values.

On the other hand, while the above standard values are effective only for the case where an impurity in an amide compound shows a given UV absorption or reacts with potassium permanganate, it cannot contribute to detection of other impurities.

The presence of a lactam other than a desired lactam and an amide compound is undesirable because they may inhibit polymerization and deteriorate physical properties of a polymer. However, when there are, as impurities, a lactam and/or an amide compound having a structure different from that of a product lactam, the above standard values are not always changed, so that it is necessary to establish a method for detecting and assaying the impurities and measures for reducing them.

PRIOR ART REFERENCES

Patent References

Patent Reference No. 1: Japanese Laid-open Patent Publication No. 2006-219470.
Patent Reference No. 2: International Publication No. WO 07/125,002.
Patent Reference No. 3: Japanese Laid-open Patent Publication No. 2008-156277.
Patent Reference No. 4: Japanese Laid-open Patent Publication No. 2008-162935.
Patent Reference No. 5: Japanese Laid-open Patent Publication No. 1976-041376.
Patent Reference No. 6: Japanese Examined Patent Publication No. 1977-012198.
Patent Reference No. 7: International Publication No. WO 08/096,873.
Patent Reference No. 8: International Publication No. WO 09/069,522.
Patent Reference No. 9: German Patent No. 1,253,716.
Patent Reference No. 10: German Patent No. 1,004,616.
Patent Reference No. 11: East German Patent No. 75083.
Patent Reference No. 12: U.S. Pat. No. 5,496,941.
Patent Reference No. 13: Japanese Laid-open Patent Publication No. 2009-298706.
Patent Reference No. 14: Japanese Laid-open Patent Publication No. 2006-528649.
Patent Reference No. 15: Japanese Laid-open Patent Publication No. 2004-099585.

Problem to be Solved by the Invention

An objective of the present invention is to provide a process for producing an amide compound by Beckmann rearrangement of an oxime, wherein a higher-quality amide compound is produced without generating byproducts such as ammonium sulfate in a large amount.

Means for Solving Problem

The present invention relates to the followings.

[1] A process for producing an amide compound, comprising:
reacting a ketone and hydroxylamine in the presence of an organic solvent to give an oxime (hereinafter, referred to as an oxime-forming step),
conducting Beckmann rearrangement of the oxime using a Beckmann rearrangement catalyst to give an amide compound (hereinafter, referred to as a rearrangement step), and
separating the amide compound thus produced and the solvent, and recycling the separated solvent into the oxime-forming step (hereinafter, referred to as a solvent-recycling step);
wherein an amount of each of a halide, an aldehyde compound, an alcohol compound and a nitrile compound contained in the solvent separated in the solvent-recycling step and recycled into the oxime-forming step is controlled to an amount of 0.4 mol % or less based on the ketone as the starting material.

[2] The process for producing an amide compound as described in [1], wherein an amount of each of an aldoxime compound and the amidoxime compound contained in the reaction solution in the oxime-forming step is controlled to an amount of 0.4 mol % or less based on the oxime.

[3] The process for producing an amide compound as described in [1], wherein the Beckmann rearrangement catalyst contains a halogen atom.

[4] The process for producing an amide compound as described in [1], wherein the organic solvent is an aromatic hydrocarbon.

[5] The process for producing an amide compound as described in [1], wherein the ketone is cyclododecanone.

[6] A lactam comprising double-bond-containing impurities in 15 ppm by weight or less.

[7] A process for producing the lactam as described in [6], comprising:
reacting a cyclic ketone and hydroxylamine to give an oxime represented by formula (1):

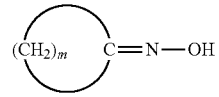

(1)

wherein m denotes an integer of three or more; and
conducting Beckmann rearrangement of the oxime using a Beckmann rearrangement catalyst to give a lactam;
wherein the rearrangement catalyst is a compound having the following moiety:

(2)

wherein Z denotes a P, N, S, B or Si atom, X denotes a halogen atom, and Z is bound to, in addition to X, one or two or more atoms or groups, or
an aromatic-ring-containing compound meeting all of the following conditions (i) to (iii); and
purifying one or more of compounds selected from the group consisting of a cyclic ketone, an oxime and a lactam by hydrogenation and/or crystallization;
(i) the aromatic-ring-containing compound contains, as an aromatic-ring member, at least one carbon atom which contains a halogen atom as a leaving group,
(ii) the aromatic-ring-containing compound contains, as an aromatic-ring member, at least three of either or both heteroatoms and carbon atoms having an electron-withdrawing group, and
(iii) two of the heteroatoms and/or carbon atoms having an electron-withdrawing group are at the ortho- or para-position to the carbon atom having a halogen atom as a leaving group.

[8] The process for producing the lactam as described in [7], wherein the cyclic ketone is purified by hydrogenation.

[9] The process for producing the lactam as described in [7] or [8], wherein the oxime is purified by crystallization.

[10] The process for producing the lactam as described in any one of [7] to [9], wherein the oxime is purified by hydrogenation.

[11] The process for producing the lactam as described in any one of [7] to [10], wherein the lactam prepared by Beckmann rearrangement of the oxime is purified by hydrogenation.

[12] The process for producing the lactam as described in any one of [7] to [11], wherein the lactam is laurolactam.

[13] A lactam comprising impurities having a cyclic bridge structure in 50 ppm by weight or less.

[14] The lactam as described in [13], wherein the impurities having a cyclic bridge structure are lactams having a dicyclic and/or a tricyclic ring structures.

[15] A process for producing a lactam by Beckmann rearrangement of a cycloalkanone oxime, wherein impurities having a cyclic bridge structure in a Beckmann rearrangement reaction solution are contained in 300 ppm by weight or less based on a lactam as a desired product.

[16] The process for producing a lactam as described in [15], wherein the impurities having a cyclic bridge structure are amide compounds having a dicyclo and/or a tricyclic ring structures.

[17] The process for producing a lactam as described in [15] or [16], wherein the cycloalkanone oxime is produced by reacting a cycloalkanone with hydroxylamine.

[18] The process for producing a lactam as described in [17], wherein the cycloalkanone is produced from an addition reaction product of butadiene.

[19] The process for producing a lactam as described in [17] or [18], wherein the ketone having a cyclic bridge structure is contained in the cycloalkanone in 500 ppm by weight or less.

[20] The process for producing a lactam as described in [19], wherein the ketone having a cyclic bridge structure is a ketone having a dicyclic ring structure and/or a ketone having a tricyclic ring structure.

[21] The process for producing a lactam as described in any one of [17] to [20], wherein the cycloalkanone is a cycloalkanone having 8 to 20 carbon atoms, which is purified by recrystallization.

[22] The process for producing a lactam as described in any one of [15] to [21], wherein the lactam is laurolactam.

Advantage of the Invention

In accordance with the present invention, an amide compound can be produced in a high yield using a small amount of a catalyst, by removing byproducts and their precursors which cause deterioration in activity of a Beckmann rearrangement catalyst, from a solvent. Furthermore, in accordance with the present invention, a high-quality amide compound with a high purity can be provided by a convenient method.

DESCRIPTION OF EMBODIMENTS

The present invention contributed to identify impurities causing deterioration in activity of a Beckmann rearrangement catalyst, impurities causing increase in a light transmittance difference and impurities causing reduction of a polymerization rate of an amide compound, and to find methods for removing these impurities. The present invention relates to a process for producing a higher-quality amide compound, particularly a lactam according to the following first to third aspects.

A first aspect of the present invention relates to a method for identifying and removing impurities causing reduction in a conversion of a Beckmann rearrangement reaction.

A second aspect of the present invention relates to a method for identifying and removing impurities having a double bond as substances causing increase in a light transmittance difference of an amide compound.

A third aspect of the present invention relates to a method for removing impurities having a cyclic bridge structure.

First, there will be described features of impurities in each aspect and methods for removing them. The matters common to the first to third aspects will be described later.

Impurities Inhibiting a Beckmann Rearrangement Reaction

The first aspect of the present invention provides a method for identifying and removing impurities causing reduction in a conversion of a Beckmann rearrangement reaction.

An amide compound is produced by a production process comprising:

(1) an "oxime-forming step" for producing a corresponding oxime; and (2) a "rearrangement step" for producing an amide compound by a Beckmann rearrangement reaction of the oxime using a Beckmann rearrangement catalyst. Here, it is preferable to further conduct a "solvent-recycling step" for separating a reaction solution after the Beckmann rearrangement reaction into an amide compound and a solvent, where the latter is recycled to the oxime-forming step.

We have investigated influence of impurities in a reaction solution for a Beckmann rearrangement reaction in the rearrangement step, on the reaction. Consequently, we have found that an aldoxime, an amidoxime and an alcohol inhibit the Beckmann rearrangement reaction (see Example A). When a solvent is recycled by the solvent-recycling step after a Beckmann rearrangement reaction, it is preferable to avoid accumulation of the substances inhibiting a Beckmann rearrangement reaction in a solvent and contamination of a recycled solvent by the substances.

It is considered that an aldoxime, an amidoxime and an alcohol are contained in a reaction solution for a Beckmann rearrangement reaction due to the following causes.

It is known that an aldoxime and an amidoxime are formed by a reaction of hydroxylamine with an aldehyde and a nitrile, respectively (Kyoritsu Shuppan Co., Ltd., "Chemical Dictionary (Kagaku Daiziten)", compact edition, 34th issue, Vol. 1, Jun. 1, 1993, p. 244 and p. 418). It is known that a nitrile is formed by a dehydration reaction of an aldoxime (Kyoritsu Shuppan Co., Ltd., "Chemical Dictionary", compact edition, 34th issue, Vol. 2, Jun. 1, 1993, p. 99 to p. 100) and an aldehyde is formed by hydrolysis of R—$CHCl_2$ (Kyoritsu Shuppan Co., Ltd., "Chemical Dictionary", compact edition, 34th issue, Vol. 1, Jun. 1, 1993, p. 412). Furthermore, for R—$CHCl_2$, Kyoritsu Shuppan Co., Ltd., "Chemical Dictionary", pocket edition, 34th issue, Vol. 1, Jun. 1, 1993, p. 1071 describes that dichloromethylbenzene corresponding to R—$CHCl_2$ is formed from toluene and phosphorous trichloride.

It is known that an alcohol is formed by hydrolysis of R—$CH_2Cl$ or alkaline decomposition of an aldehyde (Kyoritsu Shuppan Co., Ltd., "Chemical Dictionary", compact edition, 34th issue, Vol. 8, Jun. 1, 1993, p. 466).

Probably, the aldoxime, the amidoxime and the alcohol described above which inhibit a Beckmann rearrangement reaction would be, therefore, formed from these reactions.

Practically, in a combination of a catalyst and a solvent which can be used in a Beckmann rearrangement reaction, for example, thionyl chloride diluted with toluene at room temperature, benzyl chloride, benzal chloride and benzaldehyde are detected by gas chromatography. It can be inferred that a series of reactions for forming the aldoxime and the amidoxime described above proceed during each process for forming an amide compound.

A common solvent is frequently used in the rearrangement step and the oxime-forming step. It is, therefore, preferable to prevent contamination of a recycled solvent in the solvent-recycling step, by an aldoxime, a nitrile and an aldehyde as precursors for the aldoxime, and chlorides such as R—$CH_2Cl$ and R—$CHCl_2$. Furthermore, for avoiding accumulation of an alcohol, it is necessary to prevent contamination of a recycled solvent not only by the alcohol itself but also by a chloride and an aldehyde. By removing these compounds, a route for forming the above substances inhibiting a Beckmann rearrangement reaction can be blocked, and an amide compound can be stably produced using a small amount of a Beckmann rearrangement catalyst.

An acceptable accumulation amount of the substances inhibiting a Beckmann rearrangement reaction vary depending on the type of a ketone as a starting material in an oxime-forming step, the type and the amount of a Beckmann rearrangement catalyst in a rearrangement step, the type of a solvent and the like. For example, when cyclododecanone is used as a ketone as a starting material in an oxime-forming step, thionyl chloride is used as a Beckmann rearrangement catalyst in a rearrangement step and toluene is used as a solvent, the amount of an amidoxime as a byproduct contained in an oxime solution fed from the oxime-forming step to the rearrangement step is preferably 0.4 mol % or less, more preferably 0.1 mol % or less based on the amount of ketone as the starting material.

When the amount of an amidoxime in a rearrangement reaction solution is too large in a rearrangement step, a small amount of a catalyst cannot promote the rearrangement reaction to completion, resulting in remaining oxime. The Beckmann rearrangement reaction can be completed by increasing the amount of the Beckmann rearrangement catalyst, but it is undesirable because a large amount of the catalyst is needed.

An aldoxime and an alcohol are less influential to a rearrangement reaction in comparison with an amidoxime, so that they can be contained as long as their content is in the similar range of the level of an acceptable amount of the amidoxime.

As described above, an amidoxime and an aldoxime as byproducts are formed in the oxime-forming step. Therefore, for avoiding influence on a rearrangement reaction, an amount of each of a chloride, an aldehyde, an alcohol and a nitrile contained in a recycled solvent by a solvent-recycling step is controlled to preferably 0.4 mol % or less, more preferably 0.1 mol % or less based on the amount of a ketone as a starting material involved in oxime-forming.

The above byproducts can be removed so as to be an acceptable level by the method as described below.

A reaction solution after a Beckmann rearrangement reaction (hereinafter, referred to as a "rearrangement solution") is "post-treated" generally by a separation means such as filtration, concentration, distillation, extraction, crystallization, recrystallization, adsorption and column chromatography or combination thereof (detailed later), and some of the above byproducts are removed by the post-treatment. The solution can be washed with water or an alkali or treated with an acid for hydrolysis and removal by extraction of the above byproducts. For example, a nitrile can be hydrolyzed using a strong acid or base such as sulfuric acid and sodium hydroxide to be converted into a carboxylic acid.

After the post-treatment, the rearrangement solution is separated into a solvent and an amide compound in a solvent-recycling step and the solvent is recycled to an oxime-forming step. In the solvent-recycling step, a component derived from a leaving group in a Beckmann rearrangement catalyst, a residual Beckmann rearrangement catalyst, byproducts and the like which are generated in the rearrangement step and dissolved in the reaction solution are removed.

In the solvent-recycling step, a method for separating a solvent and an amide compound that is a desired product includes distillation, extraction, crystallization or recrystallization, distillation is generally employed. Here, the solvent-recycling step controls a content of impurities in a recycled solvent to within the range of the above acceptable level.

When a solvent is collected and impurities are removed by distillation in the solvent-recycling step, the byproducts derived from a solvent (for example, benzyl chloride, benzal chloride, benzaldehyde, benzyl alcohol, benzonitrile and the like when a solvent is toluene) generally have a boiling point closer to the solvent than the byproducts derived from a ketone as a reaction material (for example, 1-chlorododecane, lauronitrile, 12-chlorododecanenitrile and the like when a ketone is cyclododecanone), and, therefore, it is important to avoid contamination by the byproducts derived from a solvent. Collection of a solvent by distillation can be conducted by one distillation run, but it is more preferable that a plurality of distillation runs can be combined to return a fraction containing byproducts to the previous distillation step for preventing collection loss of a solvent and to prevent accumulation of byproducts by partly discharging the byproducts for purifying the solvent. Furthermore, it is also preferable that in order to facilitate separation/removal, the byproducts are converted into substances uninfluential to the rearrangement reaction or easily separable compounds by, for example, acid treatment, alkali treatment, oxidation, reduction or the like in the post-treatment of the rearrangement solution. For example, hydrolysis of a nitrile into a carboxylic acid by acid treatment or alkali treatment, and reduction of an aldehyde into an alcohol are included.

Methods for Preventing Increase in a Light Transmittance Difference and Impurities Causing Increase in a Light Transmittance Difference The second aspect of the present invention provides an amide compound with a light transmittance difference of preferably 35% or less, more preferably less than 35% and a production process therefor. We have also identified impurities causing increase in a light transmittance difference.

Light Transmittance Difference of an Amide Compound

When an amide compound is used as a starting material for a polymer, the presence of a polymerization inhibiting substance, a substance deteriorating physical properties and a substance causing degradation and coloration becomes disadvantageous. Evaluation measures for them include a light transmittance difference (a differential light transmittance, hereinafter referred to as an "LT. diff."), a UV value and a PAN value. Here, a light transmittance difference is one of standard values for quality of an amide compound, which is an absorbance difference at 410 nm between a 0.00909 N solution of potassium permanganate in methanol containing a sample and that free from the sample.

Even after the above post-treatment or distillation purification of the rearrangement solution, an amide compound, particularly a lactam, may not have a light transmittance difference of preferably 35% or less, more preferably less than 35%, further preferably 25% or less, and thus may have unsatisfactory quality for some applications. While acid treatment, alkali treatment, oxidation treatment, purification by extraction and purification by crystallization as generally used methods for purifying an amide compound such as a lactam were attempted, significant reduction in an LT. diff. was not observed.

We infer that when a rearrangement catalyst described later, particularly catalyst a or catalyst b (catalyst a and catalyst b will be detailed later) is used in the rearrangement step, increase in a light transmittance difference is caused by impurities formed in relation to the catalyst, that is, an oxime, a halide of a solvent and an aldehyde, an olefin, an aldoxime and the like generated in sequential reactions including solvent recycling.

We have found that first an amide compound, particularly a lactam can be purified by hydrogenation after distillation purification or without distillation purification to give a highly pure lactam, particularly laurolactam with an LT. diff. of 35% or less (see Example B). A method for hydrogenation purification of an amide compound will be described later.

Impurities Having a Double Bond

Furthermore, we have analyzed a laurolactam obtained by distillation purification by gas chromatography-mass spectrometry and have found that there is correlation between a concentration of dodeceno-12-lactam (there are several isomers) as an impurity having a double bond and a light transmittance difference (see Example C). Examples of an impurity having a double bond in a Beckmann rearrangement reaction include dodeceno-12-lactam when a ketone as a starting material is cyclododecanone, and hexeno-6-lactam when the ketone is cyclohexanone.

By controlling a content of these impurities having a double bond, an amide compound having a light transmittance difference (LT. diff.) of preferably 35% or less can be obtained. An acceptable level of these impurities in an amide compound is preferably 15 ppm or less, more preferably 10 ppm or less. If a concentration of the impurities is higher than the acceptable level, a light transmittance difference becomes over 35%.

A process for producing an amide compound involves an oxime-forming step and a rearrangement step as described above, and generally, the oxime-forming step gives an oxime from a ketone as a starting material and the rearrangement step gives an amide compound from an oxime (see the scheme below). We have found that the above impurities having a double bond can be not only removed by hydrogenation purification of the amide compound but also reduced to their acceptable level by at least one purification process selected from hydrogenation purification of the amide compound, crystallization purification or hydrogenation purification of the oxime, and hydrogenation purification of the ketone as a starting material, which results in giving a high-purity amide compound. There will be described hydrogenation purification of an amide compound, hydrogenation purification of a ketone, hydrogenation purification of an oxime and crystallization purification of an oxime.

Production of an Amide Compound

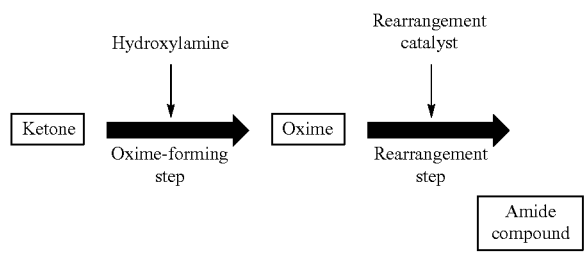

Hydrogenation Purification of an Amide Compound

In terms of hydrogenation purification of an amide compound, a reaction mixture containing an amide compound formed by a rearrangement step (rearrangement solution) or a rearrangement solution after post-treatment such as washing with water and/or washing with an alkali as shown in Reference Example B5 described later for removing a remaining catalyst and/or a catalyst residue in the rearrangement solution can be used as it is, for hydrogenation. In this case, the presence of a rearrangement solvent allows for hydrogenation at a low temperature. When a rearrangement solution is purified by hydrogenation without post-treatment, a hydrogenation catalyst may be poisoned due to remaining of a rearrangement catalyst and/or a catalyst residue, depending on the type of the rearrangement catalyst. Furthermore, when a rearrangement solvent susceptible to hydrogenation is contained, there may be restrictions to the type of a hydrogenation catalyst and the conditions of hydrogenation. A reaction mixture after the post-treatment such as washing with water and/or washing with an alkali is less influenced by a rearrangement catalyst and/or a catalyst residue in comparison with a rearrangement solution without being post-treated, but there may be restrictions to the type of a hydrogenation catalyst, the conditions of hydrogenation and the like.

Alternatively, in terms of hydrogenation purification of an amide compound, a rearrangement solution after removal of a solvent used in a Beckmann rearrangement reaction or a reaction mixture purified by distillation after removal of a solvent can be hydrogenated as it is (that is, solvent-free). A reaction mixture after distillation purification is not influenced by a catalyst residue, and the type of a hydrogenation catalyst and the hydrogenation conditions can be selected from wide alternatives, and is, therefore, preferable as an object of hydrogenation. Furthermore, it can be dissolved in a solvent tolerant to the conditions of hydrogen reduction and then can be hydrogenated. Suitable examples of the solvent include aliphatic alcohols having 1 to 3 carbon atoms (for example, methanol and ethanol) and aliphatic hydrocarbons (for example, hexane, heptane, octane and cyclododecane), and depending on the hydrogenation conditions, aromatic hydrocarbons (for example, benzene, toluene and xylene) can be used.

A hydrogenation process is conducted in the presence of a hydrogenation catalyst. Here, a hydrogenation catalyst is used as a suspended bed in which a catalyst is suspended in a system, an immobilized bed and other styles which are generally used in a hydrogenation process. Typically, a hydrogenation catalyst used is a bulk catalyst, a supported catalyst or the like.

A suitable hydrogenation catalyst can be derived from one or combination of metals selected from the group consisting of iron (Fe), nickel (Ni), copper (Cu), cobalt (Co), ruthenium (Ru), rhodium (Rh), palladium (Pd), osmium (Os), iridium (Ir), gold (Au) and platinum (Pt).

A catalyst carrier can be selected from, for example, activated charcoal (C), alumina ($Al_2O_3$), silica ($SiO_2$), titanium oxide ($TiO_2$), magnesium oxide (MgO), zirconium oxide ($ZrO_2$) or zinc oxide (ZnO), calcium oxide (CaO), diatomaceous earth, clay mineral, lanthanum oxide ($La_2O_3$) or a rare-earth metal oxide such as cerium oxide ($Ce_2O_3$). Furthermore, a mixture of these oxides or a complex oxide thereof can be used. Furthermore, silicates or phosphates of magnesium, aluminum or boron can be used as a catalyst carrier.

A hydrogenation catalyst can be particulate or powdery, and as a particulate catalyst, spherical, cylindrical, amorphous or special-shaped can be used.

Specific examples include palladium or platinum supported on activated charcoal (Pd/C, Pt/C), Ni/alumina (sulfur tolerant Ni/$Al_2O_3$ and so on) and Ni/diatomaceous earth, and a so-called stabilized nickel catalyst in which activity of nickel is controlled (a catalyst stabilized by dry reduction of a nickel salt supported on purified diatomaceous earth) is inexpensive and easily-handled is thus a particularly preferable catalyst. Furthermore, sulfur tolerant Ni/$Al_2O_3$ and on the like that is pre-treated such as pre-reduction is used.

Hydrogenation can be conducted in one step using the catalyst alone, or in multisteps. For example, when a rearrangement solution or a reaction mixture after washing with water and/or washing with an alkali is hydrogenated, hydrogenation can be conducted in a processing vessel using a catalyst highly tolerant to poisoning such as sulfur and chlorine (so-called a "guard catalyst") and a processing vessel using a hydrogenation catalyst generally used which are connected in series.

For a supported catalyst, a concentration of a catalyst element is, as a metal weight, preferably 0.01 to 80% by weight, more preferably 0.1 to 50% by weight based on the total weight of catalysts.

An additive which improves catalyst activity can be further added; for example, zirconium, manganese, copper, chromium, titanium, molybdenum, tungsten, iron or zinc.

These additives are added in an amount corresponding to generally 50% by weight or less, preferably 0.1 to 10% by weight based on a catalytically active metal.

Production of these supported or unsupported catalysts are described in many literatures such as Ullmann's Encyclopedia of Industrial Chemistry, 5th edition, Vol. A5, pp. 348 to 350.

Hydrogenation is conducted under atmospheric pressure or a pressure of 0.1 to 10 MPa, preferably 0.1 to 5 MPa, more preferably 0.1 to 1 MPa.

In general, a temperature of hydrogenation is preferably 50° C. or higher and 170° C. or lower and it is further preferably 70° C. or higher and 160° C. or less because polymerization of an amide compound can be prevented. For example, when an amide compound is $\epsilon$-caprolactam, the temperature is more preferably lower than 160° C. For example, when an amide compound is laurolactam and hydrogenation is conducted in a nonsolvent system, the temperature is preferably higher than a melting point of laurolactam (152° C.).

Hydrogenation Purification of a Ketone Compound

When a ketone is used as a starting material in an oxime-forming step, a produced ketone may be contaminated with an impurity having a double bond. For example, the impurity having a double bond is cyclohexenone when the cyclic ketone is cyclohexanone, and it is cyclododecenone when the cyclic ketone is cyclododecanone.

Although hydrogenation of a ketone compound can be conducted using a solvent, direct hydrogenation in a nonsolvent system is preferable for avoiding hydrogenation of a solvent.

A hydrogenation catalyst can be selected from those derived from the metals described in the hydrogenation of an amide compound, and among these transition metals, particularly palladium (Pd), ruthenium (Ru) and platinum (Pt) are preferable for removal of impurities because they exhibit good selective hydrogenation properties for a double bond without causing hydrogenation of a cyclic ketone.

These transition metals can be used as a salt or complex dissolved in a ketone or a solution thereof, or supported on a carrier.

A catalyst carrier can be selected from, for example, charcoal (C) or alumina ($Al_2O_3$), silica ($SiO_2$), titanium oxide ($TiO_2$), magnesium oxide (MgO), zirconium oxide ($ZrO_2$) or zinc oxide (ZnO), calcium oxide (CaO), barium oxide (BaO), diatomaceous earth, clay mineral, lanthanum oxide ($La_2O_3$) or a rare-earth metal oxide such as cerium oxide ($Ce_2O_3$).

The hydrogenation conditions vary depending on the types of a ketone and a catalyst; for example, when a ketone is cyclododecanone and a catalyst metal is palladium (Pd) and/or ruthenium (Ru) and/or platinum (Pt), a ratio of catalyst metal/ketone is preferably 0.001 to 1% by weight, more preferably 0.01 to 0.5% by weight, a hydrogen partial pressure is preferably 0.1 to 20 MPa, more preferably 0.2 to 10 MPa, a reaction temperature is preferably 75 to 200° C., more preferably 90 to 150° C., and a reaction time (an average residence time when a continuous flow apparatus) is preferably 1 minute to 10 hours, more preferably 10 minutes to 3 hours.

When hydrogenation is too mild in a certain combination of the above hydrogenation conditions, impurities disadvantageously remain. When hydrogenation is too severe, ketone hydrogenation leads to generation of an alcohol and the like, leading to a lower yield while an additional purification apparatus is required for removing byproducts, which is undesirable.

Hydrogenation Purification of an Oxime

A method for hydrogenation purification of a solution containing an oxime (hereinafter, referred to as an "oxime oil") is also effective in reduction of a light transmittance difference of a lactam.

A catalyst, a solvent and the conditions for hydrogenation purification of an oxime oil are as described for hydrogenation of an amide compound. Here, for a solvent, a solvent used in an oxime-forming step or a rearrangement solvent is preferably used in this process in the light of a process configuration.

Crystallization Purification of an Oxime

Furthermore, an oxime can be subjected to crystallization purification to remove impurities. There are no particular restrictions to a solvent in crystallization purification of an oxime as long as it is inert to an oxime and can appropriately solve an oxime. Examples include organic acids such as acetic acid, propionic acid and trifluoroacetic acid; nitriles such as acetonitrile, propionitrile and benzonitrile; amides such as formamide, acetamide, dimethylformamide (DMF) and dimethylacetamide; aliphatic hydrocarbons such as hexane, heptane, octane and cyclododecane; aromatic hydrocarbons such as benzene, toluene and xylene; halogenated hydrocarbons such as chloroform, dichloromethane, dichloroethane, carbon tetrachloride, chlorobenzene and trifluoromethylbenzene; nitro compounds such as nitrobenzene, nitromethane and nitroethane; esters such as ethyl acetate and butyl acetate; fluoroalcohols such as hexafluoroisopropyl alcohol and trifluoroethanol; and lower aliphatic alcohols such as methanol, ethanol and propanol.

Among these, lower aliphatic alcohols such as methanol, ethanol and propanol are preferable as a solvent because impurities can be dissolved in a high solubility and less impurities remain in precipitated crystals.

However, a lower aliphatic alcohol may react with a rearrangement catalyst, making a Beckmann rearrangement reaction less active, and, therefore, depending on selection of a rearrangement catalyst, crystallized crystals must be dried for removing the alcohol solvent.

Impurities Having a Cyclic Bridge Structure and a Method for Removing them

The third aspect of the present invention provides a method for identifying impurities having a cyclic bridge structure contained in a lactam and removing them to give a high-purity lactam.

When a lactam is used as a starting material for a polymer, the presence of a polymerization inhibiting substance, a substance deteriorating physical properties and a substance causing degradation and coloration becomes disadvantageous. As evaluation measures for them, a light transmittance difference, a UV value and a PAN value are used. Although specific substances deteriorating these evaluation indices have not been identified, they are believed to be compounds having a remaining double bond, compounds having an aldehyde group and compounds having a carbonyl group from comparison of the results of impurity analysis in a cycloalkanone as a starting material with the above evaluation indices of a lactam (see, for example, Japanese laid-open patent publication No. 2004-99585).

When these are contained as impurities, for example, they can be converted into a desired lactam or separable impurities by hydrogenation as described in the second aspect because they have a chemically active functional group or bond.

We have found that when a cycloalkanone is used as a starting material in an oxime-forming step for producing a lactam, there are impurities remaining even after the above hydrogenation purification (see Example D).

We extracted impurities detectable by gas chromatography (GC) with a solvent in which a desired lactam has a low solubility and it is slightly soluble and then concentrated them, and then a gas chromatography-mass spectrum (GC-Mass) of each impurity was deliberately analyzed. Consequently, we detected a plurality of impurities having a molecular weight smaller than the desired lactam by 2 or 4, and fragment M/Z smaller than that of the desired lactam by 2 or 4. Most of these impurities exhibited, even after hydrogenation, no changes in a retention time of GC (gas chromatography) analysis, parent peaks in GC-Mass analysis and fragmentation. The results imply that these are amide compounds having a dicyclo or tricyclic ring structure that have a cyclic bridge structure.

An impurity which is an amide compound having a cyclic bridge structure and does not have any other reactive bond such as a functional group and/or a double bond (hereinafter, referred to as an "impurity having a bridge structure") is not detected by the above evaluation method based on a light transmittance difference or the like, and remains in a lactam compound as an impurity even after hydrogenation. Furthermore, if the impurity is contained in a trace amount, even direct analysis of a solution of a product lactam by gas chromatography is ineffective for detection due to difficulty in separation of the impurity from the lactam.

In the third aspect of the present invention, a concentration of these impurities having a bridge structure in a lactam is preferably 50 ppm by weight or less, further preferably 30 ppm by weight or less. A higher concentration of the impurities is undesirable because a polymerization degree of an amide compound tends not to increase in polymerization of the lactam, leading to contamination with a polymer having a cyclic side chain.

We have analyzed a cycloalkanone oxime produced from a cycloalkanone and hydroxylamine, and a cycloalkanone as its starting material in order to understand origin of generation of an impurity having a cyclic bridge structure. Consequently, we have detected a ketone having a corresponding cyclic bridge structure in the cycloalkanone as a starting material.

In terms of a ketone having a cyclic bridge structure in a cycloalkanone as a starting material, US Patent Application No. 2010/0191018 has described that it contains a ketone having a dicyclic ring structure, which is formed due to intramolecular aldol condensation of a cyclic diketone and that the impurity having a dicyclic ring structure is an impurity which cannot be removed by distillation purification.

Meanwhile, as described in Example D later, a main impurity in a lactam is an amide having a tricyclic ring structure. Not only the presence of an amide having a tricyclic ring structure but also a ketone having a tricyclic ring structure as a possible starting material of the former are unknown. However, for instance, in the case of cyclododecanone, we can assume one generation pathway that bicyclo[6,4,0]cyclododeca-4,10-diene is formed as a byproduct during trimerization of butadiene, whose oxidation then gives a diketone, and then, the diketone is subjected to intramolecular aldol condensation to give the ketone having a tricyclic ring structure.

For reducing an impurity having a cyclic bridge structure in a lactam, it is, therefore, necessary to purify a cycloalkanone as a starting material to remove a ketone having a corresponding cyclic bridge structure. We have investigated a method for purifying a starting cycloalkanone and have found a method for removing an impurity having a cyclic bridge structure in a starting cycloalkanone, which is related to reduction of an impurity having a cyclic bridge structure in a lactam. Specifically, for reducing an impurity having a cyclic bridge structure in a lactam, the amount of a ketone having a cyclic bridge structure in a cycloalkanone used in the reaction is preferably 500 ppm by weight or less. There will be described below a method for removing an impurity having a cyclic bridge structure in a lactam.

Method for Removing a Ketone Having a Cyclic Bridge Structure in a Cycloalkanone As described above, for removing an impurity having a cyclic bridge structure in a lactam, it is effective to remove a ketone having a cyclic bridge structure in a cycloalkanone as a source. After intense investigation, we have found that a ketone having a cyclic bridge structure in a cycloalkanone as an impurity can be removed by recrystallization from a solvent in which a subject cycloalkanone is moderately dissolved with a low solubility. There are no particular restrictions to an applied solvent as long as it moderately dissolves a subject cycloalkanone with a low solubility and furthermore, is inert to the cycloalkanone, and it can be selected from chain hydrocarbons, alicyclic hydrocarbons, hydrogenated condensed aromatic compounds, aromatic hydrocarbons, ethers and esters. A basic solvent such as an amine is undesirable because it forms a shiff base with a cycloalkanone. An alcohol may form an acetal or hemiacetal, depending on the types of a ketone and the alcohol and the process conditions, leading to limitation to its application. In general, when both ketone and alcohol are sterically less hindered, their use under acidic conditions must be avoided. A ketone and an aldehyde do not affect recrystallization itself, but are undesirable because if a solvent remains, they may react with hydroxylamine to form an oxime other than a desired product. The amount of a solvent is preferably 5% by weight or more and 80% by weight or less, more preferably 10% by weight or more and 50% by weight or less based on a cycloalkanone. A too small amount of a solvent is undesirable because a solution of an impurity remains between crystals of a purified cycloalkanone, leading to a remaining impurity. A too large amount of a solvent is also undesirable because a one-pass yield of recrystallization is reduced and a large apparatus is required for collection and recycling of the solvent, resulting in energy waste.

In recrystallization of the present invention, a temperature during dissolving a cycloalkanone is a melting point of the cycloalkanone or lower. If a temperature is higher than a melting point of the cycloalkanone, it fuses incorporating an impurity during precipitation of crystals. A temperature during precipitating crystals can be any temperature equal to or higher than a melting point of the solvent, but a temperature below zero is undesirable because the use of a cooling medium is required, leading to a higher cost. There are no particular restrictions to the amount of a recrystallization solvent as long as it is the amount capable of dissolving a cycloalkanone or more at a dissolving temperature, but the minimal required amount is preferable in the light of improving a one-pass yield.

Recrystallization can be conducted under ambient pressure, increased pressure or reduced pressure, but it is generally conducted at ambient pressure. By recrystallization of a cycloalkanone, a content of a ketone having a cyclic bridge structure as an impurity is reduced to about 1/10 to 1/50 of that before recrystallization. By oxime-forming of the cycloalkanone obtained and Beckmann rearrangement, an impurity having a cyclic bridge structure in a Beckmann rearrangement reaction solution can be controlled to 300 ppm by weight or less based on a lactam as a desired product, giving a product lactam containing an impurity having a cyclic bridge structure in 50 ppm by weight or less.

There will be a method for removing a ketone having a cyclic bridge structure, taking cyclododecanone as an example.

A preferable recrystallization solvent moderately solve cyclododecanone with a low solubility, including chain hydrocarbons such as n-hexane, n-heptane, n-octane, isooctane, n-decane and n-dodecane; alicyclic hydrocarbons such as cyclohexane, cyclopentane and cyclooctane; hydrogenated condensed aromatic compounds such as tetralin and decalin; aromatic hydrocarbons such as benzene, toluene and xylenes; ethers such as diethyl ether; and esters such as ethyl acetate and butyl acetate. An alcohol such as methanol and ethanol can be also used for purification of cyclododecanone. Among these recrystallization solvents, preferred are chain aliphatic hydrocarbons having 6 to 8 carbon atoms such as n-hexane, n-heptane and n-octane; alicyclic hydrocarbons having 5 to 8 carbon atoms such as cyclopentane, cyclohexane and cyclooctane; and aliphatic alcohol having 1 to 2 carbon atoms such as methanol and ethanol, whereby a high one-pass yield can be obtained in recrystallization, and in the light of collection of a solvent, further preferred are n-heptane, n-octane and methanol.

A temperature during dissolving cyclododecanone is preferably 61° C., a melting point of cyclododecanone, or lower. If the temperature is higher than a melting point of cyclododecanone, it fuses incorporating an impurity during precipitation of crystals. A temperature during precipitating crystals can be any temperature equal to or higher than a melting point of the solvent, but a temperature below zero is undesirable because the use of a cooling medium is required, leading to a higher cost. There are no particular restrictions to the amount of a recrystallization solvent as long as it is the amount capable of dissolving cyclododecanone or more at a dissolving temperature, but the minimal required amount is preferable in the light of improving a one-pass yield. For example, when a chain hydrocarbon or aliphatic alcohol as described above is used as a solvent, the amount of the solvent is preferably 15% by weight or less, more preferably 10% by weight or less based on the total weight of cyclododecanone and the solvent.

Recrystallization is generally conducted at ambient pressure. By recrystallization of cyclododecanone, a content of a ketone having a cyclic bridge structure as an impurity is reduced to about 1/10 to 1/50. Oxime-forming by reacting cyclododecanone thus produced with hydroxylamine, followed by Beckmann rearrangement to give laurolactam, in which a level of an impurity having a bridge structure is 50 ppm by weight or less.

Laurolactam produced as described above can provide high-purity Nylon 12 having improved physical properties with a high polymerization degree.

As described above, in terms of the processes for producing an amide compound or a lactam according to the aspects, the first aspect is mainly characterized in that an amount of each of a halide, an aldehyde compound, an alcohol compound and a nitrile compound contained in a solvent recycled to an oximation step is controlled to an amount of 0.4 mol % or less based on a ketone as a starting material;

the second aspect is mainly characterized in that at least one compound selected from the group consisting of a ketone, an oxime and an amide compound is purified by hydrogenation and/or crystallization;

the third aspect is mainly characterized in that a ketone is recrystallized, and a plurality of the purification methods in these aspects can be combined. Thus, a higher-quality amide compound or lactam can be obtained.

Next, there will be described an amide compound and a process for producing the amide compound of the present invention, particularly, an oxime-forming step for producing an oxime, a rearrangement step of Beckmann rearrangement of the oxime using a Beckmann rearrangement catalyst, and purification of an amide compound which is usually conducted after the rearrangement step. Unless otherwise indicated, the description below is commonly applied to the first to the third aspects.

Amide Compound

An amide compound of the present invention is preferably, but not limited to, a lactam, more preferably a lactam represented by formula (3).

(3)

wherein n is 3 to 20, preferably 3 to 15. Generally, n is 5, 7, 8, 9, or 11 when a lactam is industrially used as a starting material for a polymer or copolymer used in a yarn, a fiber, a film and the like. Among these lactams, a lactam with n=11, that is, laurolactam, is particularly useful because it provides a polymer exhibiting excellent flexibility, water resistance and solvent resistance. Furthermore, in the present invention, a macrocyclic lactam with n=7 or more is suitably used.

There will be described each step in a process for producing an amide compound.

Oxime-Forming Step

In the present invention, an oxime-forming step denotes a step for producing an oxime. An oxime produced by the oxime-forming step can be appropriately selected, depending on an amide compound to be produced. When an amide compound to be produced is a lactam, an oxime corresponding to it is represented by formula (1).

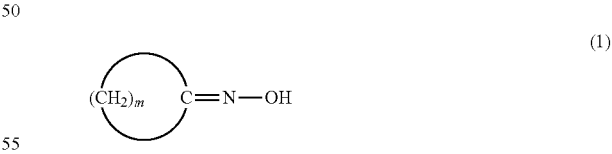

(1)

wherein m denotes an integer of 3 or more.

In the formula, m is 3 to 20, preferably 3 to 15. Specific examples include cyclobutanone oxime, cyclohexanone oxime, cycloheptanone oxime, cyclooctanone oxime, cyclononanone oxime, cyclodecanone oxime, cycloundecanone oxime, cyclododecanone oxime, cyclotridecanone oxime, cyclotetradecanone oxime, cyclopentadecanone oxime, cyclohexadecanone oxime, cyclooctadecanone oxime and cyclononadecanone oxime. Among these, cyclohexanone oxime, cyclooctanone oxime, cyclononanone oxime, cyclodecanone oxime, cycloundecanone oxime and cyclododecanone oxime are useful oximes, and cyclooctanone oxime, cyclononanone oxime, cyclodecanone oxime, cycloundecanone oxime and cyclododecanone oxime are more preferable, and cyclododecanone oxime is particularly preferable.

In formula (1), a ring can have a substituent or can be fused with another ring. Examples of a substituent which can be attached to the ring include alkyl, alkenyl, alkynyl, cycloalkyl, cycloalkenyl, aryl, aralkyl and aromatic or non-aromatic heterocycle.

Alkyl can be, for example, alkyl having 1 to 20 carbon atoms, preferably alkyl having 1 to 12 carbon atoms, further preferably alkyl having 2 to 8 carbon atoms. Specific examples include methyl, ethyl, propyl, isopropyl, butyl, isobutyl, s-butyl, t-butyl, pentyl, isopentyl, hexyl, isohexyl, heptyl, octyl, nonyl, decyl, dodecyl and pentadecyl.

Alkenyl can be, for example, alkenyl having 2 to 20 carbon atoms, preferably alkenyl having 2 to 12 carbon atoms, further preferably alkenyl having 2 to 8 carbon atoms. Specific examples include vinyl, allyl, 1-propenyl, 1-butenyl, 1-pentenyl and 1-octenyl.

Alkynyl can be, for example, alkynyl having 2 to 20 carbon atoms, preferably alkynyl having 2 to 12 carbon atoms, further preferably alkynyl having 2 to 8 carbon atoms. Specific examples include ethynyl and 1-propynyl.

Cycloalkyl can be, for example, cycloalkyl having 3 to 20 carbon atoms, preferably cycloalkyl having 3 to 15 carbon atoms. Specific examples include cyclopropyl, cyclobutyl, cyclopentyl, cyclohexyl, cycloheptyl, cyclooctyl and cyclododecyl.

Cycloalkenyl can be, for example, cycloalkenyl having 3 to 20 carbon atoms, preferably cycloalkenyl having 3 to 15 carbon atoms. Specific examples include cyclopentenyl, cyclohexenyl and cyclooctenyl.

Examples of aryl include phenyl and naphthyl.

Examples of aralkyl include benzyl, 2-phenylethyl and 3-phenylpropyl.

Examples of aromatic or non-aromatic heterocycle include 2-pyridyl, 2-quinolyl, 2-furyl, 2-thienyl and 4-piperidinyl.

An oxime can be produced by any of the following processes:

(i) reacting a ketone with an aqueous solution of hydroxylamine;

(ii) reacting a ketone with ammonia and hydrogen peroxide in the presence of a catalyst such as titanosilicate;

(iii) reacting a compound having a methyl or methylene group with a nitrite ester or nitrite salt in the presence of an N-hydroxyimide compound and a compound produced by introducing a protecting group (for example, an acyl group such as acetyl) to a hydroxyl group in the N-hydroxyimide compound (for example, Japanese laid-open patent publication No. 2009-298706); and (iv) photonitrosating an alkane;

and in the present invention, the production process (i) is most suitably employed.

In the production process (i) for an oxime, since hydroxylamine is unstable, a method where a hydroxylamine salt undergoes double decomposition in the presence of a ketone in a reaction vessel and then a liberated hydroxylamine and ketone are reacted is generally employed for safety operation. Here, preferably, a ketone and hydroxylamine are reacted in equimolar amounts.

In the production process (iii) for an oxime, an N-hydroxyimide compound is derived from an aliphatic polycarboxylic anhydride (cyclic anhydride) or aromatic polycarboxylic anhydride (cyclic anhydride) such as N-hydroxysuccinimide, N-hydroxyphthalimide, N,N-dihydroxypyromellitic diimide, N-hydroxyglutalimide, N-hydroxy-1,8-naphthalene dicarboxylic imide and N,N'-dihydroxy-1,8,4,5-naphthalene tetracarboxylic diimide.

Ketone

There are no particular restrictions to a ketone used in the production processes (i) and (ii) for an oxime, and it can be appropriately selected depending on a desired amide compound. For example, when a desired amide compound is a lactam, a corresponding oxime can be a compound represented by formula (4).

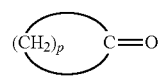

(4)

wherein p is 3 to 20, preferably 3 to 15. More preferably p is 5, 7, 8, 9, 10, 11 and particularly preferably, p is 11. Furthermore, p is preferably 7 or more.

Examples of a ketone represented by formula (4) include cyclobutanone, cyclopentanone, cyclohexanone, cycloheptanone, cyclooctanone, cyclononanone cyclodecanone, cyclododecanone, cyclotridecanone, cyclotetradecanone, cyclopentadecanone, cyclohexadecanone, cyclooctadecanone and cyclononadecanone. Among these, cyclohexanone, cyclooctanone, cyclononanone cyclodecanone, cycloundecanone and cyclododecanone are useful ketones, and cyclooctanone, cyclononanone, cyclodecanone, cycloundecanone and cyclododecanone are more preferable and cyclododecanone is particularly preferable.

In formula (4), a ring can have a substituent or can be fused with another ring. The substituent can be selected from those listed in the description of the oxime represented by formula (1).

One or two or more ketones as starting materials can be selected for use.

Process for Producing a Ketone

A process for producing a ketone as a starting material can be oxidation of a corresponding hydrocarbon. A hydrocarbon to be oxidized can be a saturated or unsaturated hydrocarbon. For oxidation of an unsaturated hydrocarbon, when a carbon-carbon unsaturated bond remains after oxidation, the unsaturated bond must be converted into a saturated bond by hydrogenation. An oxidizing agent used for oxidation of a hydrocarbon is generally oxygen (molecular oxygen) and the air, but hydrogen peroxide, nitrous oxide or the like can be also used.

For example, a cyclic ketone can be produced by a common process where a corresponding cycloalkane is oxidized by the air. When a cycloalkane is oxidized by the air, a cyclic ketone (cycloalkanone) is obtained as a mixture with a cyclic alcohol (cycloalkanol), so that the cycloalkanol in the mixture is dehydrogenated to be converted into a cyclic ketone (cycloalkanone).

For example, when cyclododecanone is produced as a ketone, cyclododecanone can be produced by employing a process where cyclododecatriene is hydrogenated into cyclododecane followed by air oxidation to give a mixture of cyclododecanone/cyclododecanol and cyclododecanol is then dehydrogenated.

When a cyclic ketone is produced, it can be also produced by a process where an unsaturated compound which is a starting material for producing an alkane is oxidized while its double bond remains intact and then the double bond is hydrogenated. Examples of a method employed can include a process where cyclododecatriene is oxidized by nitrous oxide to give cyclododecadienone, whose remaining double bond is then hydrogenated to produce cyclododecanone (for example, Japanese laid-open patent publication No. 2007-506695), a process where cyclododecatriene is oxidized by hydrogen peroxide to give epoxy cyclododecadiene, whose double bond is then hydrogenated to give epoxy cyclododecane, which is further isomerized to provide cyclododecanone (for example, Japanese laid-open patent publication No. 2000-256340, No. 2000-026441, No. 2001-302650, and No. 2001-226311). Alternative examples of such a process include a process where double bonds in benzene are partly hydrogenated to give cyclohexene, which is hydrated to give cyclohexanol, which is then dehydrogenated to provide cyclohexanone, and a process where isopropylbenzene is oxidized to give phenol, which is then hydrogenated to provide cyclohexanone. When a cyclic ketone is produced by any of these processes, a ketone having a double bond and/or a ketone having a cyclic bridge structure that can generate impurities in a lactam may remain or generate.

When a cycloalkanone is produced as a ketone, a cyclic compound as its starting material can be prepared by employing an addition reaction between dienes. For example, when cyclododecanone is produced, a starting material is cyclododecatriene in any of the above processes, and it is prepared by trimerization of butadiene. Specifically, for example, an addition reaction of butadiene is conducted while adjusting activity of a catalyst prepared from a titanium halide and an alkylaluminum halogenide (so-called Ziegler catalyst) and then, the catalyst is appropriately inactivated to produce cyclododecatriene (for example, German Patent No. 1050333, Japanese laid-open patent publication No. 1994-254398, No. 1993-124982 and No. 1993-070377). Likewise, for example, cyclooctadiene can be produced by dimerization of butadiene.

Hydroxylamine

Since hydroxylamine used in the production process (i) for an oxime is unstable, it is produced and sold as an aqueous solution of an acid salt of hydroxylamine such as hydroxylamine sulfate or hydroxylamine carbonate. Before conducting a reaction, a base such as aqueous ammonia is added to the solution to liberate hydroxylamine, which is used for the reaction. Although an aqueous solution of hydroxylamine preliminarily liberated can be fed in the production process of an oxime, generally an aqueous solution of an acid salt of hydroxylamine (preferably, sulfate) and a base (preferably, aqueous ammonia) are fed into an oxime-forming reaction vessel, to liberate hydroxylamine in the reaction vessel.

Solvent for an Oxime-Forming Step In a production step of an oxime, a solvent is used. Preferably, an oxime is highly dissolvable in the solvent. A suitable solvent depends on the type of an oxime, and when the oxime is cyclododecanone oxime, a solvent having a solubility parameter $\delta$ defined by the following equation of 7.5 to 13.0 is preferable, and 8.0 to 12.5 is particularly preferable, in which cyclododecanone oxime is highly dissolvable.

Here, a solubility parameter $\delta$ indicates strength of intermolecular bonding force such as hydrogen bond, and the larger it is, the higher polarity is. Substances having close solubility parameters exhibit higher mutual compatibility. The parameter can be calculated from the data including $\Delta(\text{delta})E^V$, a normal boiling point and a density, and $\Delta E^V$ can be estimated from a molecular structure.

$$\delta = (\Delta E^V/V)^{1/2}$$

wherein $\delta$ represents a solubility parameter, $\Delta E^V$ represents a change in internal energy of evaporation and V represents a molar volume (see "Chemistry Handbook, Basic I, Revised 5th edition", edited by The Chemical Society of Japan, Maruzen Co., Ltd., p. 770.).

In addition, as a solvent used in a production step of an oxime, a solvent which may react with a starting material during production of the oxime, even if the solvent exhibits good dissolvability of the oxime, is preferably precluded. For example, when a ketone or aldehyde is used as a solvent, it reacts with hydroxylamine to form a ketoxime or aldoxime. When a nitrile is used as a solvent, it reacts with hydroxylamine to form an amidoxime. An amide also, when being used as a solvent, forms an adduct with hydroxylamine. When an amine is used as a solvent, it reacts with a ketone to form a Schiff base. Therefore, these solvents, although these exhibit good dissolvability of an oxime, must be precluded from a solvent herein.

The use of an identical solvent in the oxime-forming step and in a rearrangement step described later is preferable because it eliminates the necessity for solvent exchange and simplifies a process, leading to reduction in equipment expenses and energy cost. Here, a solvent in the rearrangement step preferably 1) dissolves an amide with a high solubility, 2) is inert to an amide, and 3) is inert to a Beckmann rearrangement catalyst.

When an identical solvent is used in the oxime-forming step and the rearrangement step, there may be substantially no problems for 1) and 2). It is because generally, a solubility parameter of an amide compound is substantially comparable to that of a corresponding oxime and there is little difference of reactivity between them. In contrast, for 3), a catalyst used in Beckmann rearrangement has an electron-withdrawing leaving group as described later, and therefore, preferably a solvent susceptible to a nucleophilic substitution reaction is excluded. Specifically, water, alcohols, amines, mercaptans and amides are preferably excluded from a solvent. Furthermore, when a highly reactive rearrangement catalyst is used, carboxylic acids and carboxylic acid esters are preferably excluded.

In an oil/water separation step described later, preferably a solvent is easily separable, has a lower loss in an aqueous phase and is easily recovered in a solvent-recycling step.

Specifically, preferable solvents include aromatic hydrocarbons, compounds produced by hydrogenation of a condensed polycyclic hydrocarbon and alicyclic hydrocarbons (particularly, alicyclic hydrocarbons having a side chain). Preferable examples of an aromatic hydrocarbon include benzene, toluene, xylene, ethylbenzene, propylbenzene, butylbenzene, trimethylbenzene, tetramethylbenzene and cyclohexylbenzene; particularly preferably, benzene, toluene and xylene. Preferable examples of a compound produced by hydrogenation of a condensed polycyclic hydrocarbon include tetralin, decalin and dihydronaphthalene; particularly preferably tetralin and decalin. Preferable examples of an alicyclic hydrocarbon having a side chain include isopropylcyclohexane, methylcyclohexane, dimethylcyclohexane and ethylcyclohexane; particularly preferable is isopropylcyclohexane. Among these solvents, toluene or xylene is most preferable.

There are no particular restrictions to a temperature during an oxime-forming reaction, but since hydroxylamine is used as an aqueous solution, when a reaction temperature is too high, for example, the reaction at 100° C. or higher, a pressurized vessel is required. On the other hand, when a reaction temperature is too low, the reaction is slow. The oxime-forming reaction is, therefore, conducted preferably at 100° C. or less and an ambient pressure, further preferably at 60° C. or higher, and more preferably 75° C. or higher.

Reaction Apparatus for an Oxime-Forming Step

A reaction apparatus used in an oxime-forming step can be a common reaction apparatus such as a batch type reaction apparatus, a semi-batch type reaction apparatus, a tubular continuous reaction apparatus and a continuous stirred tank flow reactor, preferably a multistage continuous stirred tank flow reactor. When a multistage continuous stirred tank flow reactor is used, an aqueous solution of hydroxylamine is fed to the first tank, a ketone solution (a solution of a ketone in the above solvent) is fed to the last tank, and the aqueous phase and the oil phase are sequentially transferred to the latter and the former tanks, respectively, and desirably, the reaction completes without unreacted starting materials remaining.

Reaction Time of an Oxime-Forming Step

A reaction time of an oxime-forming step varies depending on a ketone, a solvent, reaction conditions such as a temperature and the type of a reaction vessel. When a ketone is cyclododecanone, a solvent is toluene and a multistage continuous stirred tank flow reactor is employed, a reaction time is 1 to 20 hours, preferably 5 to 15 hours. If a reaction time is too short, disadvantageously the starting materials, hydroxylamine and/or cyclododecanone remain, which must be recycled. If a reaction time is too long, a reaction vessel disadvantageously becomes larger. It is possible to add an additive such as a surfactant to improve a mass transfer rate between oil and aqueous phases and to reduce a reaction time.

Oil/Water Separation Step

In the present invention, an oil/water separation step denotes a step where a reaction solution after the oxime-forming step is separated into an oil phase and an aqueous phase and the oil phase containing an oxime is obtained. Separation into an oil and an aqueous phases is conducted using a common separation method such as standing separation, centrifugation and separation using a cyclone. In an industrial continuous step, a reaction solution is fed from a reaction apparatus of the oxime-forming step to a separation apparatus, where the solution is separated into an oil and an aqueous phases, which are then drained. Depending on the type of the reaction apparatus in the oxime-forming step, an oil and an aqueous phases can be drained from the reaction apparatus.

Then, a part of the solvent and dissolved water are removed from an oxime-containing solution obtained as an oil phase in the oil/water separation step, which is then fed to a rearrangement step. A content of water in the solution is 1000 ppm or less, preferably 500 ppm or less, more preferably 100 ppm or less. Water is removed by azeotropic distillation with the solvent and the solvent containing distilled water is recycled to the oxime-forming step.

Rearrangement Step

As described above, a dehydrated oxime-containing solution after the oil/water separation step is fed to a rearrangement step. In the rearrangement step, an amide compound is produced from the oxime by a Beckmann rearrangement reaction using a Beckmann rearrangement catalyst. Here, one or two or more oximes can be selected for use.

Beckmann Rearrangement Catalyst

As a Beckmann rearrangement catalyst, a compound having at least two electron-withdrawing leaving groups can be used. For example, it can be a compound having at least two structures represented by formula (5). This also includes a compound where a plurality of Xs are attached to A. When a plurality of A-Xs are present, these can be identical or different.

$$-A-X \quad (5)$$

wherein A represents C (carbon atom), P, N, S, B or Si and X represents an electron-withdrawing leaving group, wherein A is attached to, in addition to X, one or two or more atoms or groups.

The electron-withdrawing leaving group for X can be a common eliminable functional group; for example, a halogen atom (fluorine, chlorine, bromine and iodine), a —OR group (R represents an organic group), a carboxyl group, an amino group and a sulfonyloxy group. Among these functional groups, a halogen atom is preferable and a chlorine atom is more preferable.

There are no particular restrictions to a Beckmann rearrangement catalyst as long as it is a compound having at least two structures represented by formula (5) in one molecule (including a compound where a plurality of Xs are attached to A), and it can be a cyclic or acyclic compound.

Specific examples of a Beckmann rearrangement catalyst in the present invention include phosphazene compounds (phosphazene derivatives), phosphate ester compounds including polyhalophosphates (phosphate ester derivatives), phosphine compounds (phosphine derivatives), imide compounds (imide derivatives), sulfonyl or sulfinyl compounds (sulfonyl or sulfinyl derivatives), silane compounds (silane derivatives), cyclic compounds containing a silicon atom as a ring member, phosphorous halides, halosulfuryls and mixtures thereof.

Examples of a phosphazene compound include halophosphazene derivatives such as hexachlorophosphazene, hexafluorophosphazene and hexabromophosphazene.

Examples of a phosphate ester compound include dimethyl chlorophosphate, diethyl chlorophosphate, 2-chloro-1,3,2-dioxaphosphorane-2-oxide, methyl dichlorophosphate, ethyl dichlorophosphate, diphenyl chlorophosphate, 1,2-phenylene phosphorochloridate and phenyl dichlorophosphate.

Examples of a phosphine compound include halophosphine derivatives such as chlorodimethylphosphine, chlorodiethylphosphine, chlorodipropyl phosphine, chlorodiphenylphosphine, dichloroethylphosphine, dichlorobutylphosphine and dichlorohexylphosphine.

Examples of an imide compound include succinimide derivatives such as N-halosuccinimide derivatives (for example, N-chlorosuccinimide, N-bromosuccinimide, N-iodosuccinimide and N-fluorosuccinimide); phthalimide derivatives such as N-halophthalimide derivatives (for example, N-chlorophthalimide, N-bromophthalimide, N-iodophthalimide and N-fluorophthalimide); maleimide derivatives such as N-halomaleimide derivatives (for example, N-chloromaleimide, N-bromomaleimide, N-iodomaleimide and N-fluoromaleimide); hydantoin derivatives such as halohydantoin derivatives (for example, 1,3-dichloro-5,5-dimethylhydantoin and 1,3-dibromo-5,5-dimethylhydantoin); and cyanuric acid derivatives including cyanuric acid halide derivatives such as trichlorotriazine (also referred to as trichlorocyanuric acid or cyanuric chloride) and dichlorocyanuric acid sodium salt.

Examples of a sulfonyl or sulfinyl compound include sulfonyl halide derivatives such as methanesulfonyl chloride, ethanesulfonyl chloride, propanesulfonyl chloride, trichloromethanesulfonyl chloride, trifluoromethanesulfonyl chloride, benzenesulfonyl chloride, toluene sulfonyl chloride, nitrobenzenesulfonyl chloride, chlorobenzenesulfonyl chloride, fluorobenzenesulfonyl chloride and naphthalenesulfonyl chloride; sulfanyl chloride; and thionyl chloride.

Examples of a silane compound include halosilane derivatives such as chlorotriphenylsilane, dichlorodiphenylsilane and phenyltrichlorosilane.

Examples of a cyclic compound containing a silicon atom as a ring member include halogenated silicon nitride.

Examples of a phosphorous halide include phosphorous trichloride and phosphorous pentachloride.

Examples of a halosulfuryl include sulfuryl chloride.

Catalyst a or catalyst b described below can be used as a Beckmann rearrangement catalyst in the present invention, and in particular, its use is preferable in the second aspect of the present invention.

Catalyst a is represented by formula (2), which is included in a Beckmann rearrangement catalyst represented by formula (5).

$$-Z-X \quad (2)$$

wherein Z represents P, N, S, B or Si, and X represents halogen, wherein Z is attached to, in addition to X, one or two or more atoms or groups.

For a compound represented by formula (5) in which A is carbon atom, catalyst b shown below is particularly suitable.

Catalyst b is an aromatic-ring-containing compound meeting all of the following conditions (b1) to (b3).

(b1) It contains, as an aromatic-ring member, at least one carbon atom which contains a halogen atom as a leaving group.

(b2) It contains, as an aromatic-ring member, at least three of either or both heteroatoms and carbon atoms having an electron-withdrawing group.

(b3) two of the heteroatoms or the carbon atoms having an electron-withdrawing group are in ortho or para position to the carbon atom having a halogen atom as a leaving group.

The phrase "contains at least three of either or both heteroatoms and carbon atoms having an electron-withdrawing group" means that the compound may contain, as aromatic-ring member atoms, at least three or more of heteroatoms or carbon atoms having an electron-withdrawing group alone or in combination.

An aromatic ring in an aromatic-ring containing compound means an aromatic hydrocarbon ring such as a benzene ring and an aromatic heterocycle. Examples of an aromatic-hydrocarbon-ring-containing compound include monocyclic hydrocarbon rings such a benzene ring; and, as polycyclic hydrocarbon rings, condensed rings such as a naphthalene ring, an anthracene ring, a fluorene ring, a phenanthrene ring, azulene ring and pyrene ring, as well as a biphenyl ring, a terphenyl ring and a triphenyl ring. Examples of an aromatic heterocycle include five-membered rings such as a pyrrol ring, a furan ring, a thiophene ring, an imidazole ring, a pyrazole ring, a triazole ring, a tetrazole ring, an oxazole ring, an isoxazole ring, a thiazole ring, an isothiazole ring and furazan; and six-membered rings such as a pyridine ring, a pyrazine ring, a pyrimidine ring, a pyridazine ring and a triazine ring, particularly preferably nitrogen-containing aromatic rings. Examples of an aromatic-ring-containing compound having the aromatic ring suitably include, in addition to monocyclic-aromatic-ring-containing compounds having the aromatic ring, condensed heterocyclic compounds such as an indole ring, a benzoimidazole ring, a benzotriazole ring, a quinoline ring, a bipyridyl ring and a phenanthroline ring. Among these, suitable examples can include a benzene ring, a pyridine ring and a triazine ring. An atom as a constituting member for the aromatic ring can be any atom as long as it meets all of the above conditions (b1) to (b3).

Examples of a halogen atom as a leaving group in the above conditions (b1) to (b3) include a fluorine atom, a chlorine atom, a bromine atom and an iodine atom, and among these, a chlorine atom is preferable.

While there are no particular restrictions to an electron-withdrawing group in the above conditions (b1) to (b3) as long as it is a known electron-withdrawing group, examples include cyano, trifluoromethyl, trichloromethyl, nitro, halogen, carbonyl and sulfonyl, and among these, cyano and nitro are preferable.

Specific examples of a heteroatom in the above conditions (b1) to (b3) include nitrogen, oxygen, sulfur and silicon, and among these, nitrogen is particularly preferable.

Examples of an aromatic-ring-containing compound meeting all of the above conditions (b1) to (b3) include benzene-ring compounds such as 4-chloro-3,5-dinitrobenzonitrile, 4-fluoro-3,5-dinitrobenzonitrile, 4-bromo-3,5-dinitrobenzonitrile, 4-chloro-1,3,5-trinitrobenzene, picryl chloride, picryl bromide and picryl fluoride, and among these, suitable examples are 4-chloro-3,5-dinitrobenzonitrile and picryl chloride. Furthermore, examples of a heterocyclic compound include 2-chloro-3,5-dinitropyridine, 2-bromo-3,5-dinitropyridine, 2-fluoro-3,5-dinitropyridine, trichlorotriazine (also referred to as isocyanuric chloride, cyanuric chloride, trichlorotriazole or trichloroisocyanuric acid), tribromotriazine and trifluorotriazine, and among these, suitable examples are 2-chloro-3,5-dinitropyridine and trichlorotriazine.

Among these, a compound having conjugated π-electrons between at least two structures represented by formula (5) or a compound in which a plurality of Xs are attached to A is suitable as a Beckmann rearrangement catalyst of the present invention, and trichlorotriazine, thionyl chloride, phosphorous trichloride and phosphorous pentachloride can be more suitably used.

Pre-Preparation of a Beckmann Rearrangement Catalyst

There will be detailed pre-preparation of a Beckmann rearrangement catalyst.

In the rearrangement step, the above Beckmann rearrangement catalyst and the total amount of an oxime can be blended and then, a rearrangement reaction can be conducted at a temperature of the rearrangement step, but in some cases, more preferably a rearrangement catalyst is pre-prepared to be used for a rearrangement reaction. Here, pre-preparation of a catalyst means that at least part of an oxime and a Beckmann rearrangement catalyst are blended and reacted at a temperature lower than a temperature of a rearrangement step.

When catalyst a or catalyst b, particularly catalyst a is used, preferably a lactam is produced by a process having a pre-preparation step of blending the catalyst with at least part of an oxime and reacting them and a rearrangement reaction step of conducting a rearrangement reaction of the oxime at a temperature higher than that of the pre-preparation step.

The pre-preparation step gives a catalytically active species. For example, we have confirmed that when thionyl chloride is used as catalyst a and cyclododecanone oxime is used as an oxime, cyclododecanone O-azacyclotridecen-2-yl oxime hydrochloride represented by formula (6) (here, this compound denotes a compound represented by formula (6), a stereoisomer other than the compound represented by formula (6) or a mixture as a combination thereof) is formed as a catalytically active species.

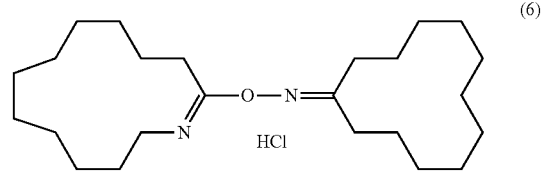 [SMILES: C1CCCCCC(=NO/C2=N/CCCCCCCCCCC2)CCCCC1 ; Cl]

(6)

Pre-Preparation Process from an Oxime and Catalyst a

An oxime and catalyst a are blended at a temperature lower than a temperature of a Beckmann rearrangement reaction of the oxime (hereinafter, referred to as "pre-preparation"). An objective of the pre-preparation step is to form a species exhibiting catalytic activity to a Beckmann rearrangement reaction (hereinafter, referred to as a "catalytically active species"). Here, when part of the oxime is used for pre-preparation, it is not necessary to use an identical oxime in the pre-preparation step and the rearrangement reaction, but preferably an identical oxime is used.

Blending Ratio in a Pre-Preparation Step

When part of an oxime is used for pre-preparation, a blending ratio of the oxime and catalyst a (molar ratio of (oxime/catalyst a)) varies depending on selection of the oxime and catalyst a; for example, when cyclododecanone oxime and thionyl chloride are selected as an oxime and catalyst a, respectively, the ratio is preferably 0.5 or more and 10.0 or less, more preferably 1.0 or more and 5.0 or less, further preferably more than 1 and 5.0 or less, particularly preferably 1.5 or more and 3.0 or less.

The amount of catalyst a for blending is preferably 0.01 mol % to 20 mol %, more preferably 0.1 mol % to 5 mol % based on the total amount of the oxime used in the pre-preparation step and the rearrangement step.

If the amount of the oxime is too small, most of thionyl chloride as catalyst a does not form a catalytically active species, so that pre-preparation becomes ineffective.

If the amount of the oxime is too large, a pre-preparation apparatus becomes disadvantageously large. As the example of the case, when cyclododecanone oxime and thionyl chloride are used as an oxime and catalyst a, respectively, a large amount of a solvent is required and thus a pre-preparation apparatus becomes disadvantageously large for preventing solid precipitation or occlusion in the pre-preparation step. This is because cyclododecanone oxime has a higher melting point than a catalytically active species and is less soluble in a solvent described later at a temperature described later. Furthermore, it is undesirable because a cost for solvent recovery and an energy cost for recycling increase. For avoiding such inactivation, the use of an excessive amount of an oxime must be avoided.

Temperature of a Pre-Preparation Step

There are no particular restrictions to a temperature of the pre-preparation, but it is conducted at a reaction temperature of a Beckmann rearrangement reaction described later or lower, preferably 50° C. or lower, further preferably 30° C. or lower, most preferably room temperature or lower. If a pre-preparation temperature is too high, disadvantageously most of the catalytically active species is converted to a lactam while, for example, when thionyl chloride is used, hydrogen chloride is released, leading to deterioration in catalyst activity. There are no particular restrictions to the lower limit of a preparation temperature as long as a reaction system does not coagulate, but when a temperature is 10° C. or lower, further 0° C. or lower, the use of a cooling system is required, which is uneconomic.

Solvent for a Pre-Preparation Step

A solvent can be used in the pre-preparation step of the present invention. Suitable solvents for each aspect are as follows.

When a rearrangement catalyst and at least part of an oxime are used for pre-preparation, there are no particular restrictions to a solvent used as long as it does not react with a rearrangement catalyst or the oxime. When catalyst a is used, examples of a solvent which can be used include organic acids such as acetic acid, propionic acid and trifluoroacetic acid; nitriles such as acetonitrile, propionitrile and benzonitrile; amides such as formamide, acetamide, dimethylformamide (DMF) and dimethylacetamide; aliphatic hydrocarbons such as hexane, heptane, octane and cyclododecane; aromatic hydrocarbons such as benzene, toluene and xylene; halogenated hydrocarbons such as chloroform, dichloromethane, dichloroethane, carbon tetrachloride, chlorobenzene and trifluoromethylbenzene; nitro compounds such as nitrobenzene, nitromethane and nitroethane; esters such as ethyl acetate and butyl acetate; fluoroalcohols such as hexafluoroisopropyl alcohol and trifluoroethanol; and mixtures of these solvents.

When catalyst a is used, a solvent other than water, alcohols, amines, mercaptans and amides can be used.

When thionyl chloride is used as catalyst a, there are no particular restrictions to a solvent used in pre-preparation as long as it does not react with thionyl chloride or an oxime. Examples of a solvent which can be used include nitriles such as acetonitrile, propionitrile and benzonitrile; aliphatic hydrocarbons such as hexane, heptane, octane and cyclododecane; aromatic hydrocarbons such as benzene, toluene and xylene; halogenated hydrocarbons such as chloroform, dichloromethane, dichloroethane, carbon tetrachloride, chlorobenzene and trifluoromethylbenzene; nitro compounds such as nitrobenzene, nitromethane and nitroethane; and mixtures thereof. Among these, aliphatic hydrocarbons and aromatic hydrocarbons are particularly suitable solvents because a rate of a Beckmann rearrangement reaction can be easily controlled in the pre-preparation step.

Compounds having an active hydroxyl group or an analogous functional group including organic bases such as amines, water, alcohols and mercaptans, as well as carboxylic acids and carboxylic acid ester to which thionyl chloride acts as a chlorinating agent cannot be used.

There are no particular restrictions to the amount of a solvent in the pre-preparation step, and when cyclododecanone oxime is used as an oxime and toluene is used as a solvent, a weight concentration of the oxime is preferably 1% or more and 60% or less, particularly preferably 3% or more and 30% or less, depending on a temperature and a size of a reaction vessel. If the amount of the solvent is too small, an oxime is inadequately dissolved while if the amount of the solvent is too large, solvent recovery disadvantageously becomes more troublesome, which is uneconomical.

Time of a Pre-Preparation Step

When pre-preparation is conducted using a rearrangement catalyst and at least part of an oxime, a time taken for the pre-preparation varies depending on the type of catalyst a, a blending ratio of an oxime/catalyst a, a preparation temperature, the amount of a solvent and so on, and preferably, but not limited to, 1 min or more and 24 hours or less, further preferably 1 min or more and 10 hours or less.

The lower limit of a time taken for pre-preparation depends on a time for homogeneously mixing a rearrangement catalyst, and a too shot time of pre-preparation is undesirable because results such as a yield of a lactam formed by a Beckmann rearrangement reaction are not improved compared to those obtained by direct addition of a rearrangement catalyst to a rearrangement reaction vessel. A too long preparation time is also undesirable because a catalytically active species is gradually partly converted into an inactive compound, leading to reduction in a rearrangement rate.

For example, when thionyl chloride is used as catalyst a, cyclododecanone oxime is used as an oxime, a blending ratio is 1, toluene is a solvent, a preparation temperature is 25° C. and a concentration of cyclododecanone oxime in pre-preparation is 3% by weight, the prepreparation time is suitably 1 min or more and 10 hours or less, further preferably 1 min or more and 3 hours or less, and when a blending ratio is more than 1, a preparation time can be longer.

Industrially, the upper limit of a time taken for pre-preparation depends on the size of a reaction vessel, but if a residence time is more than 3 hours, an apparatus becomes too large, so that in some cases it is preferably less than 3 hours.

Apparatus Used for Pre-Preparation

In the present invention, pre-preparation can be conducted in any common mixing tank such as a batch type, a semi-batch type and a continuous type tanks. Alternatively, as long as a predetermined residence time can be ensured, blending can be conducted in a piping. A mixing style can be mixing by a mixing impeller or in-line mixing using, for example, a static mixer.

Beckmann Rearrangement Reaction

There will be described a Beckmann rearrangement reaction.

In a Beckmann rearrangement reaction, when part of an oxime is used in a pre-preparation step, the remaining oxime is added to a rearrangement reaction. Assuming that all the reactants after the pre-preparation are used, the amount of a Beckmann rearrangement catalyst used in the Beckmann rearrangement reaction is, preferably 0.01 mol % to 20 mol %, more preferably 0.1 mol % to 5 mol % based on the total amount of the oxime used in the pre-preparation step and the rearrangement reaction step. A too small amount of a Beckmann rearrangement catalyst is undesirable because a Beckmann rearrangement reaction ceases. A too large amount of a Beckmann rearrangement catalyst is undesirable from an industrial point of view because a catalyst cost increases and also a cost for post-treatment of a catalyst or recycling increases.

When catalyst b is used, pre-preparation may not be sometimes required, depending on the reaction conditions of Beckmann rearrangement. The amount of catalyst b is preferably 0.0001 to 1 moles, more preferably 0.0005 to 0.5 moles, further preferably 0.001 to 0.2 moles to one mole of an oxime.

Co-Catalyst

In the present invention, a Lewis acid or Broensted acid can be added as a co-catalyst to improve a rearrangement reaction rate. In particular, a Lewis acid is preferable because it can increase a rearrangement reaction rate without promoting hydrolysis of an oxime, particularly cyclododecanone oxime.

Examples of a Lewis acid include halides of one or two or more metals selected from the group consisting of zinc, cobalt, antimony, tin and bismuth; specifically, zinc fluoride, zinc chloride, zinc bromide, cobalt fluoride, cobalt chloride, cobalt bromide, antimony pentafluoride, antimony pentachloride, antimony pentabromide, tin tetrafluoride, tin tetrachloride, tin tetrabromide, bismuth trifluoride, bismuth trichloride and bismuth tribromide. Zinc chloride, cobalt chloride, antimony pentachloride, tin tetrachloride and bismuth trichloride are suitable, and zinc chloride is particularly preferable because it is inexpensive and prominently increases a reaction rate.

Examples of a Broensted acid include inorganic acids such as sulfuric acid, hydrochloric acid and nitric acid; and organic acids including sulfonic acids such as p-toluenesulfonic acid and methanesulfonic acid.

When a co-catalyst is used, its amount is preferably 0.01 molar parts to 10 molar parts, more preferably 0.1 molar parts to 5 molar parts to a Beckmann rearrangement catalyst. If the amount of a co-catalyst is too small, it is less effective for improving a reaction rate of Beckmann rearrangement, while if it is added more than necessary, further increase in a reaction rate is not achieved.

Solvent Used in a Beckmann Rearrangement Reaction

While it is preferable that a solvent in pre-preparation is also used as a solvent in a rearrangement reaction (hereinafter, referred to as a "rearrangement solvent") for simplifying a production process, a different solvent can be used. When a different solvent is used, for example, a rearrangement solvent can be added to a pre-preparation solution followed by evaporation of a pre-preparation solvent to conduct solvent exchange into the rearrangement solvent. Alternatively, while a pre-preparation solvent and a rearrangement solvent are blended, a Beckmann rearrangement reaction can be conducted.

Conditions of a Beckmann Rearrangement Reaction

A temperature of a Beckmann rearrangement reaction is preferably 60 to 160° C., more preferably 80 to 130° C. A too low reaction temperature is undesirable because a reaction rate is reduced, resulting in termination of the reaction. A too high reaction temperature is undesirable because a Beckmann rearrangement reaction becomes so exothermic that a temperature rapidly rises and thus the reaction cannot be controlled. Furthermore, a too high reaction temperature leads to reduction in a rearrangement yield due to side reactions such as a condensation reaction and deterioration in product quality due to staining and so on.

The reaction conditions are controlled such that a reaction can be easily controlled and an excessively larger reaction vessel is not required.

A Beckmann rearrangement reaction can be conducted under reduced pressure, ambient pressure or increased pressure. Although it is not obligatory to conduct the reaction under increased pressure, the reaction can be conducted in a closed system to prevent components generated from the rearrangement catalyst (for example, when the leaving group X is a halogen atom, it is hydrogen halide) from scattering out of the reaction system. Such a closed process can be employed to eliminate the necessity for setting up additional facilities for adsorption and removal of components such as hydrogen halide generated from the rearrangement catalyst. Furthermore, generation of hydrogen halide is preferable because it is an acid which can promote the rearrangement reaction as a co-catalyst.

In the first and the second aspects of the present invention, a Beckmann rearrangement reaction is more preferably conducted by the processes described above. The third aspect of the present invention can employ, besides the processes described above, a rearrangement process where a commonly used strong acid such as sulfuric acid and fuming sulfuric acid is added or a rearrangement process where a gas containing an oxime is made passing through a solid acid to initiate rearrangement (a gas rearrangement process; see Japanese laid-open patent publication No. 2000-229939 and so on).

Apparatuses used in a Beckmann rearrangement reaction. As an apparatus used in a Beckmann rearrangement reaction, can be a commonly used reaction apparatus such as a batch type reaction apparatus, a tubular continuous reaction apparatus and a continuous stirred tank flow reactor, and a multi-stage continuous stirred tank flow reactor is suitable in the light of easy control of a reaction temperature and simple operation.

Post-Treatment of a Beckmann Rearrangement Solution

For a reaction solution obtained by a Beckmann rearrangement reaction (rearrangement solution), preferably components derived from a leaving group in a Beckmann rearrangement catalyst dissolved in the reaction solution and a residual Beckmann rearrangement catalyst are removed. These substances can be removed by separation means such as filtration, concentration, distillation, extraction, crystallization, recrystallization, adsorption and column chromatography or a combination thereof. As a particularly preferable and convenient method, a rearrangement solution is washed with water (adding water to remove the components as an aqueous solution) and/or washed with an alkali (washing with an aqueous solution of a hydroxide of an alkali metal such as sodium and potassium to remove an acidic catalyst component and so on) to remove catalyst components and so on.

Evaporation of a Solvent

After the above post-treatment, a Beckmann rearrangement solution is evaporated to remove a solvent. Here, the separated solvent can be, as described above, recycled to an oxime-forming step through a solvent-recycling step.

Distillation Purification of an Amide Compound

A common purification method such as distillation purification, crystallization/recrystallization and melt crystallization can be used for further purifying a separated amide compound, particularly a lactam. Typically, a distillation operation (including draining as a distillate fraction, draining as bottoms, rectification and so on) is preferable and a multistep combination of distillation operations is more preferable.

For the above process for producing an amide compound, particularly a lactam, there have been sequentially described the step of oxidizing an aliphatic or aromatic hydrocarbon as a starting material to produce a ketone as an intermediate material; the step of producing an oxime from the ketone; and the step of producing an amide compound from the oxime, but, if desired, a process for producing a lactam compound can be efficiently selected by combining these steps.

As described above, for example, cycloalkanone oxime can effectively give a lactam having a larger number of members by one (for example, cyclohexanone oxime gives ε-caprolactam, cyclooctanone oxime gives 8-octanelactam, and cyclododecanone oxime gives 12-laurolactam).

EXAMPLES

There will be specifically described the present invention with reference to Examples. These examples illustrate exemplary embodiments of the present invention, but the present invention is not limited to these examples.

Example A

In Reference Examples A1 and A2, a laurolactam solution obtained by a Beckmann rearrangement reaction of cyclododecanone oxime (rearrangement solution) was analyzed for impurities. Furthermore, in Examples A1 to A23 and Comparative Examples A1 to A7, influence of impurities on a conversion of cyclododecanone oxime was studied.

Reference Example A1

Analysis of Impurities in a Laurolactam Rearrangement Solution Prepared Using Thionyl Chloride as a Catalyst To a pillow type first oxime-forming reactor with a liquid-phase volume of 30 L whose inside was divided into four chambers, each of which was equipped with a mixing blade, were fed a 15% by weight aqueous solution of hydroxylamine sulfate (Wako Pure Chemical Industries, Ltd.) at 1.5 kg/h and an oil phase supplied from a second oxime-forming reactor. A reaction temperature was set to 95° C., and 25% by weight of aqueous ammonia was fed to each chamber at 32 g/h to initiate an oxime-forming reaction to give an oil phase consisting of cyclododecanone oxime and toluene.

The aqueous phase was fed to the second oxime-forming reactor. The second oxime-forming reactor was a 15 L pillow type reactor whose inside was divided into four chambers. The aqueous phase of the oxime-forming reaction solution and a 25% by weight of cyclododecanone in toluene solution at 2 kg/h (in an equimolar amount to hydroxylamine sulfate fed to the first reactor) were fed to the reactor, and a reaction temperature was set to 95° C. and a 25% by weight aqueous ammonia was fed to each chamber at 16 g/h to initiate an oxime-forming reaction. The reaction solution thus obtained was phase-separated and the oil phase was fed to the first oxime-forming reactor.

To a 20 L evaporator was placed 10 kg of the oil phase obtained in the first oxime-forming reactor, and toluene was removed by evaporation to give 5.26 kg of a solution of cyclododecanone oxime in toluene. A content of cyclododecanone oxime was quantitatively analyzed by gas chromatography, and a content of cyclododecanone oxime was 50% by weight (hereinafter, referred to as a "50% by weight cyclododecanone oxime solution"). To 5.26 kg of the resulting 50% by weight cyclododecanone oxime solution was added 18.2 g of zinc chloride, and the mixture was heated to 90° C. for dissolution (hereinafter, referred to as a "50% by weight cyclododecanone oxime/zinc chloride solution"). Separately, the 50% by weight cyclododecanone oxime solution was diluted with toluene to prepare a 20% by weight cyclododecanone oxime/toluene solution (hereinafter, referred to as a "20% by weight cyclododecanone oxime solution").

To 35 mL two neck flat-bottom flask having an overflow drain outlet were fed a 10% by weight solution of thionyl chloride (Beckmann rearrangement catalyst) in toluene at 27.15 g/h and a 20% by weight solution of cyclododecanone oxime warmed to 50° C. at 56.3 g/h, and the mixture was stirred by a stirring bar to pre-prepare a Beckmann rearrangement catalyst, which was then fallen into a reaction vessel for a Beckmann rearrangement reaction. Meanwhile, to the reaction vessel for a Beckmann rearrangement reaction was fed a 50% by weight cyclododecanone oxime/zinc chloride solution at 580 g/h. The rearrangement reaction vessel was consisted of two 160 mL CSTRs (Continuous Stirred Tank Flow Reactor), in which a heat-medium temperature in a jacket was adjusted such that a liquid temperature was to be 105° C. The reaction was continuously conducted for 10 hours.

100 g of water was added to 1 kg of the rearrangement reaction solution obtained above, and the mixture was stirred at 85° C. for 10 min for washing and allowed to stand for phase separation to give an oil phase, which was then similarly washed with 100 g of a 4% by weight aqueous solution of sodium hydroxide to remove the catalyst and its residue, to give a solution of laurolactam in toluene.

Analytical detection of the solution of laurolactam in toluene by gas chromatography showed that the solution contained 3 ppm of benzaldehyde, 6 ppm of benzyl chloride, 1 ppm of benzyl alcohol, 9 ppm of benzonitrile, 19 ppm of cyclododecene, 2 ppm of benzaldoxime, 46 ppm of 1-chlorododecane, 15 ppm of lauronitrile, 677 ppm of cyclododecanone, 293 ppm of cyclododecanone oxime, 197 ppm of 12-chlorododecanenitrile and 70 ppm of dodecanedinitrile, and a laurolactam purity was 99.35%. Here, a byproduct proportion to laurolactam was 0.0012 mol % for benzaldehyde, 0.0021 mol % for benzyl chloride, 0.0004 mol % for benzyl alcohol, 0.0038 mol % for benzonitrile, 0.005 mol % for cyclododecene, 0.0007 mol % for benzaldoxime, 0.0098 mol % for 1-chlorododecane, 0.0036 mol % for lauronitrile, 0.1618 mol % for cyclododecanone, 0.0647 mol % for cyclododecanone oxime, 0.0398 mol % for 12-chlorododecanenitrile and 0.0159 mol % for dodecanedinitrile.

Analytical detection of the solution of thionyl chloride in toluene used for pre-preparation by gas chromatography showed 27 ppm of benzaldehyde and 79 ppm of benzyl chloride, indicating that in the pre-preparation step, toluene had been already chlorinated and an aldehyde had been formed. These byproducts were formed in the amounts corresponding to 0.0005 mol % and 0.011 mol %, respectively, to laurolactam produced.

Reference Example A2

Analysis of Impurities in a Laurolactam Rearrangement Solution Prepared Using Trichlorotriazine as a Catalyst A solution of laurolactam in toluene was obtained as described in Reference Example A1, except that a catalyst fallen into a rearrangement reaction vessel was used as a 3% by weight solution of trichlorotriazine/toluene, a falling rate was 90.5 g/h and a rearrangement reaction temperature was 95° C. Analytical detection of the solution of laurolactam in toluene by gas chromatography showed that the solution contained 3 ppm of benzaldehyde, 4 ppm of benzyl chloride, 2 ppm of benzyl alcohol, 7 ppm of benzonitrile, 4 ppm of benzaldoxime, 8 ppm of 1-chlorododecanone, 22 ppm of lauronitrile, 5000 ppm of cyclododecanone, 2000 ppm of cyclododecanone oxime, 480 ppm of 12-chlorododecanenitrile and 25 ppm of dodecanedinitrile and a purity of laurolactam was 98.80%. Here, a byproduct proportion to laurolactam was 0.0013 mol % for benzaldehyde, 0.0015 mol % for benzyl chloride, 0.0009 mol % for benzyl alcohol, 0.0031 mol % for benzonitrile, 0.0015 mol % for benzaldoxime, 0.0017 mol % for 1-chlorododecanone, 0.0056 mol % for lauronitrile, 1.262 mol % for cyclododecanone, 0.4661 mol % for cyclododecanone oxime, 0.1023 mol % for 12-chlorododecanenitrile and 0.0060 mol % for dodecanedinitrile.

Examples A1 to A9 and Comparative Examples A1 to A3

Evaluation of Influence of Byproducts when a Rearrangement Reaction was Conducted Using Thionyl Chloride as a Catalyst In a flat-bottomed flask equipped with a jacket was charged 0.118 g (0.099 mmol) of a 10% by weight solution of thionyl chloride/toluene, and the mixture was cooled to 10° C. and stirred by a stirring bar. To the mixture was added 0.244 g (0.245 mmol) of a 20% by weight solution of cyclododecanone oxime/toluene prepared in Reference Example A1 while being heated to 50° C., and the mixture was pre-prepared for 10 min (a pre-preparation solution: a ratio of cyclododecanone oxime/thionyl chloride=2.5 (mol/mol)). Separately, to 6.0 g of a 50% by weight cyclododecanone oxime/zinc chloride solution prepared in Reference Example A1 (14.147 mmol of cyclododecanone oxime and 0.151 mmol of zinc chloride) were added individual byproducts detected in the laurolactam/toluene solution in Reference Example A1 such that the amount of each byproduct became 1 mol % to cyclododecanone oxime, to prepare a rearrangement reaction material solution. The rearrangement reaction material solution was heated with stirring to 105° C. to give a homogeneous solution, and the above pre-preparation solution was added (thionyl chloride/cyclododecanone oxime: 0.7 mol %, zinc chloride/cyclododecanone oxime: 0.96 mol %) and the mixture was reacted at the same temperature for 20 min. Amidoxime was not detected in the laurolactam/toluene solution in Reference Example A1. It is, however, easily formed from a nitrile compound and hydroxylamine and is too susceptible to hydrolysis to be detected. We, therefore, regarded that it was formed in a series of production steps and thus listed as a byproduct.

The evaluation results are shown in Table 1. The results show that amidoxime, aldoxime and benzyl alcohol adversely affect a rearrangement reaction while the other byproducts does not directly influence the reaction.

TABLE 1

|  | Additive | Ox conversion (%) |
|---|---|---|
| Example A1 | None | 100 |
| Example A2 | Benzaldehyde | 100 |
| Example A3 | Benzyl chloride | 100 |
| Example A4 | Benzonitrile | 100 |
| Example A5 | 1-Chlorodecane | 100 |
| Example A6 | Lauronitrile | 100 |
| Example A7 | Cyclododecene | 100 |
| Example A8 | 12-Chlorododecanenitrile | 100 |
| Example A9 | Dodecanedinitrile | 100 |
| Comparative Example A1 | Benzyl alcohol | 95.0 |
| Comparative Example A2 | Benzaldoxime | 85.0 |
| Comparative Example A3 | Benzamidoxime | 5.5 |

Ox: Cyclododecanone oxime

Examples A10 to A13 and Comparative Example A4

Influence of the Amount of Amidoxime

A reaction was conducted as described in Comparative Example A3, except that the amount of benzamidoxime was changed as shown in Table 2 (Examples A10 to A12 and Comparative Example A4). In Example A13, a molar equivalent of benzamidoxime and the amount of a pre-preparation liquid were increased. The experimental results are shown in Table 2.

TABLE 2

|  | Amount of Benzamidoxime (BAMO) BAMO/Ox (mol %) | Amount of a catalyst SOCl$_2$/Ox (mol %) | Ox conversion (%) |
|---|---|---|---|
| Example A10 | 0.12 | 0.7 | 100 |
| Example A11 | 0.20 | 0.7 | 95.5 |
| Example A12 | 0.36 | 0.7 | 78.9 |
| Example A13 | 0.36 | 1.1 | 100 |
| Comparative Example A4 | 0.80 | 0.8 | 25.7 |

Examples A14 to A22 and Comparative Examples A5 to A7

Evaluation of Influence of Byproducts when a Rearrangement Reaction is Conducted Using Trichlorotriazine as a Catalyst A reaction was evaluated as described in Examples A1 to A9 and Comparative Examples A1 to A3, except that a rearrangement catalyst was trichlorotriazine and a pre-preparation solution was 0.936 g of a 3% by weight trichlorotriazine solution. The results are shown in Table 3.

TABLE 3

| | Additive | Ox conversion (%) |
|---|---|---|
| Example A14 | None | 100 |
| Example A15 | Benzaldehyde | 100 |
| Example A16 | Benzyl chloride | 100 |
| Example A17 | Benzonitrile | 100 |
| Example A18 | 1-Chlorodecane | 100 |
| Example A19 | Lauronitrile | 100 |
| Example A20 | Cyclododecene | 100 |
| Example A21 | 12-Chlorododecanenitrile | 100 |
| Example A22 | Dodecanedinitrile | 100 |
| Comparative Example A5 | Benzyl alcohol | 97.0 |
| Comparative Example A6 | Benzaldoxime | 91.0 |
| Comparative Example A7 | Benzamidoxime | 75.5 |

Example A23

Analysis of Impurities when a Solvent after a Beckmann Rearrangement Reaction is Recycled, and Oxime-Forming and Beckmann Rearrangement Reaction are Conducted The process of Reference Example A1 provided 6 kg of a solution of laurolactam in toluene. The solution was placed in a 20 L evaporator and evaporated at 90° C. to recover toluene. The remaining laurolactam contained toluene in 0.2% by weight. The recovered toluene was simply distilled using a 30 cm Vigreux column to give 3030 g of distillation fraction and 150 g of bottoms. Analysis of the distillation fraction by GC detected 6 ppm of benzaldehyde, 18 ppm of benzonitrile, 12 ppm of benzyl chloride, 2 ppm of benzyl alcohol, 1 ppm of benzaldoxime and 20 ppm of cyclododecanone. These correspond to 0.0013 mol % of benzaldehyde, 0.0041 mol % of benzonitrile, 0.0022 mol % of benzyl chloride, 0.0004 mol % of benzyl alcohol, 0.0002 mol % of benzaldoxime, and 0.0026 mol % of cyclododecanone based on cyclododecanone fed in the oxime-forming reaction. Oxime-forming, oil/water separation, rearrangement and washing were conducted to obtain a solution of laurolactam in toluene as described in Reference Example A1, replacing the above distillation fraction with toluene described in Reference Example A1. To the solution of laurolactam in toluene was added the simple-distillation bottoms, and after recovering toluene by evaporation, the mixture was simply distilled to give a distillation fraction. These operations were repeated five times and the fifth distillation fraction was analyzed, resulting in detecting 20 ppm of benzaldehyde, 27 ppm of benzonitrile, 12 ppm of benzyl chloride, 2 ppm of benzyl alcohol, 1 ppm of benzaldoxime and 40 ppm of cyclododecanone. These correspond to 0.0044 mol % of benzaldehyde, 0.0027 mol % of benzonitrile, 0.0050 mol % of benzyl chloride, 0.0004 mol % of benzyl alcohol, 0.0002 mol % of benzaldoxime and 0.0052 mol % of cyclododecanone based on cyclododecanone fed in the oxime-forming reaction. Oxime-forming and rearrangement were conducted using the fifth distillation fraction, and the resulting solution of laurolactam in toluene was analyzed by GC for byproducts, detecting 11 ppm of benzaldehyde, 6 ppm of benzyl chloride, 1 ppm of benzyl alcohol, 15 ppm of benzonitrile, 66 ppm of cyclododecene, 2 ppm of benzaldoxime, 139 ppm of 1-chlorododecane, 46 ppm of lauronitrile, 826 ppm of cyclododecanone, 270 ppm of cyclododecanone oxime, 231 ppm of 12-chlorododecanenitrile and 66 ppm of dodecanedinitrile. Production proportions of these to laurolactam were 0.0045 mol % for benzaldehyde, 0.0021 mol % for benzyl chloride, 0.0004 mol % for benzyl alcohol, 0.0063 mol % for benzonitrile, 0.0173 mol % for cyclododecene, 0.0007 mol % for benzaldoxime, 0.0297 mol % for 1-chlorododecane, 0.0111 mol % for lauronitrile, 0.1974 mol % for cyclododecanone, 0.0569 mol % for cyclododecanone oxime, 0.0466 mol % for 12-chlorododecanenitrile and 0.0150 mol % for dodecanedinitrile, and reduction in catalyst activity or significant byproduct accumulation was not observed.

Example B

In the description below, in Reference Examples B1 and B2, cyclododecanone oxime was produced and dried. In Reference Examples B3 to B6, cyclododecanone oxime was subjected to Beckmann rearrangement in the presence of a catalyst to produce laurolactam, which was then post-treated, distilled and so on, and in each step, a light transmittance difference (LT. diff) of laurolactam was measured. In Examples B1 to B8, laurolactam produced in Reference Examples was purified by hydrogenation and a light transmittance difference (LT. diff) was measured.

Measurement of a Light Transmittance Difference (LT. diff)

A light transmittance difference (LT. diff) of laurolactam was measured by the following measuring method.

To 100 mL of a 2 wt/v % solution of a test sample of laurolactam in methanol was added 10 mL of a 0.01 N potassium permanganate solution at a temperature of 20° C. After 200 sec, the reaction mixture was transferred to a 50 mm cell and a transmittance % at 240 sec (T2, wavelength: 410 nm) was read. Here, a control was methanol.

Next, to 100 mL of methanol was added 10 mL of a 0.01N potassium permanganate solution at 20° C. After 200 sec, the mixture was transferred to a 5 mm cell and a transmittance % at 240 sec (T1, wavelength: 410 nm) was read. Here, a control was methanol.

A light transmittance difference (LT. diff) of the test sample of laurolactam was calculated by the following equation.

$$\text{Light transmittance difference (\%)} = T1 - T2$$

Reference Example B1

Production of Cyclododecanone Oxime

A 25% by weight aqueous ammonia (Wako Pure Chemical Industries, Ltd.) was added to an aqueous solution having a composition of 14.8% by weight of hydroxylamine sulfate, 9.5% by weight of sulfuric acid and 27.1% by weight of ammonium sulfate to adjust pH to 4 (neutralized amine). To the aqueous neutralized amine solution was added a 42.4% by weight aqueous solution of ammonium sulfate such that a concentration of hydroxylamine sulfate was 7.69% by weight. Then, 25383.3 g of the hydroxylamine sulfate solution thus prepared was added to a pillow type oxime reactor having a liquid-phase volume 40 L equipped with a mixing blade, and the mixture was heated to 85° C. and then 7241 g of cyclododecanone and 3113.7 g of toluene were added. A 25% by weight aqueous ammonia was continuously added such that pH became 5.8 at a temperature of 85° C. to promote the reaction. Once a hydroxylamine concentration in the aqueous layer became 1000 ppm or less, stirring and feeding of the aqueous ammonia were stopped and the mixture was allowed to stand, and the aqueous layer was drained. To the remaining oil layer were added 4127.3 g of toluene and 25022.6 g of neutralized amine and feeding of a 25% by weight aqueous ammonia was initiated to adjust pH to 5.8 at a temperature of 85° C. Once a cyclododecanone concentration became 1000 ppm or less, stirring was stopped and after standing, an aqueous layer was drained and the reaction was quenched. The obtained oil layer (cyclododecanone oxime-toluene solution) was analyzed by a Karl Fischer type moisture tester (Hiranuma Sangyo Co., Ltd., type AQ-2100 micro moisture tester) and a water content was 2000 ppm.

Reference Example B2

Drying of Cyclododecanone Oxime

To 4 kg of the solution of cyclododecanone oxime in toluene obtained in Reference Example B1 was added 800 g of toluene. The mixture was placed in a 10 L evaporator and then toluene was distilled off at 280 torr and a temperature of 110° C. to concentrate the mixture until a concentration of cyclododecanone oxime became 50% by weight. The 50% by weight solution of cyclododecanone oxime in toluene thus obtained was measured for moisture using a Karl Fischer type moisture tester in a dry box, and a water content was 350 ppm.

Reference Example B3

Production of Laurolactam (Thionyl Chloride Catalyst)

Zinc chloride was dissolved in the 50% by weight solution of cyclododecanone oxime in toluene obtained in Reference Example B2 at a temperature of 100° C. such that a concentration of zinc chloride became 1.0 mol % based on cyclododecanone oxime (the mixture is referred as a "starting material"). The mixture was fed to a multistep reaction apparatus consisting of two 500 mL separable flasks having a jacket equipped with a stirrer.

Separately, a 10% by weight solution of thionyl chloride in toluene and a cyclododecanone oxime-toluene solution which was prepared by diluting the 50% by weight solution of cyclododecanone oxime obtained in Reference Example B2 to a concentration of 20% by weight were line-mixed. Then, this mixture was fed to a catalyst pre-preparation reactor equipped with a water-cooling jacket, to prepare a catalytically active species, which was fed to the first tank. Feeding amounts of thionyl chloride and cyclododecanone oxime were 1.5 mol % and 3.75 mol %, respectively, based on cyclododecanone oxime as a starting material, and a residence time in the catalyst pre-preparation reactor was 30 min. A temperature of the rearrangement reaction tank was 105° C. and the total residence time in the first and the second tanks was 25 min.

The reaction solution obtained from the second tank in the reaction apparatus was analyzed by gas chromatography, and a conversion of cyclododecanone oxime was 100% and a yield of laurolactam was 99.7%. The reaction solution thus obtained was concentrated, and a light transmittance difference (LT. diff) of laurolactam was determined to be 66.8%.

Reference Example B4

Production of Laurolactam (Cyanuric Chloride Catalyst)

In 500 mL three-necked flask equipped with a reflux condenser were placed 20 g of cyclododecanone oxime (Tokyo Chemical Industry Co., Ltd.), 0.13 g of zinc chloride and 80 g of toluene, and the mixture was heated to a temperature of 90° C. To the three-necked flask was added dropwise a solution of 0.28 g of cyanuric chloride dissolved in 30 g of toluene via a dropping funnel. Two hours after the end of dropping, the reaction solution was transferred to a 1 L separable flask equipped with a jacket. To the mixture was added 50 g of ultrapure water, and the mixture was stirred at a temperature of 80° C. for 15 min. After allowing the mixture to stand for 15 min, the aqueous layer was drained. Then, to the mixture was added 50 g of a 1% by weight aqueous solution of NaOH, and the mixture was stirred for 15 min. After allowing the mixture to stand for 15 min, the aqueous layer was drained. This operation was further conducted twice followed by addition of 50 g of ultrapure water, and then the mixture was stirred for 15 min. Then, the mixture was allowed to stand for 15 min, and an aqueous layer was drained. The reaction solution thus obtained was concentrated and a light transmittance difference (LT. diff) of laurolactam was determined to be 69.5%.

Reference Example B5

Post-Treatment of a Rearrangement Reaction Solution

In a 1 L separable flask equipped with a jacket was placed 700 g of the reaction solution obtained in Reference Example B3, which was then heated to a temperature of 80° C. Ultrapure water in an amount of 10% by weight to a reaction solution was added, and the mixture was stirred for 15 min. Then, the mixture was allowed to stand for 15 min and the aqueous layer was drained. After this operation was repeated twice, a 1% by weight aqueous solution of sodium hydroxide in an amount of 10% by weight to the reaction solution was added and the mixture was stirred for 15 min. Then, the mixture was allowed to stand for 15 min and the aqueous layer was drained. Ultrapure water in an amount of 10% by weight to a reaction solution was added, and the mixture was stirred for 15 min. Then, the mixture was allowed to stand for 15 min and the aqueous layer was drained. After washing, the reaction solution was concentrated by a rotary evaporator. A light transmittance difference (LT. diff) of the crude lactam thus obtained was 66.8%, indicating no reduction in a light transmittance difference (LT. diff).

Reference Example B6

Rectification of Laurolactam

Laurolactam obtained in Reference Example B5 was distilled (bottom temperature: 190° C., degree of vacuum: 3 to 4 torr, reflux ratio: 1:1, Sulzer packing: 7 plates). A light transmittance difference (LT. diff) of laurolactam thus obtained was determined to be 45%.

Example B1

Laurolactam obtained in Reference Example B3 was distilled (bottom temperature: 190° C., degree of vacuum: 3 to 4 torr, reflux ratio: 1:1, Sulzer packing: 7 plates). To a 300 mL two-necked egg-plant flask were charged 3 g of laurolactam obtained after distillation (light transmittance difference (LT. diff)=44.7%), 60 g of methanol and 0.6 g of 2% by weight Pd/C (powder). The system atmosphere was substituted with hydrogen gas, and under hydrogen atmosphere, the reaction was conducted in the closed system at room temperature for 6.5 hours. At the end of the reaction, the mixture was filtrated through a membrane filter at a temperature of 90° C. The filtrate thus obtained was concentrated (recovery rate: 91%).

A light transmittance difference (LT. diff) of laurolactam thus obtained was determined to be 9%.

Example B2

To a 300 mL two-necked egg-plant flask were charged 3 g of laurolactam obtained in Reference Example B3 (light transmittance difference (LT. diff)=66.8%), 200 g of toluene and 1.2 g of 5% by weight Pd/C (powder). The system atmosphere was substituted with hydrogen gas, and under hydrogen atmosphere, the reaction was conducted in the closed system at room temperature for 24 hours. At the end of the reaction, the mixture was filtrated through a membrane filter at a temperature of 90° C. The filtrate thus obtained was concentrated (recovery rate: 91%). A light transmittance difference (LT. diff) of laurolactam thus obtained was determined to be 20%.

Example B3

To a 100 mL autoclave were charged 4 g of distilled laurolactam of Example B1 (light transmittance difference (LT. diff)=44.7%), 6 g of toluene and 1 g of 5% by weight Pd/C (powder). The system atmosphere was substituted with hydrogen gas, and at a pressure of 0.2 MPa and a temperature of 90° C., the reaction was conducted for 1 hour. At the end of the reaction, the mixture was filtrated through a membrane filter at a temperature of 90° C. The filtrate thus obtained was concentrated (recovery rate: 90%). A light transmittance difference (LT. diff) of laurolactam thus obtained was determined to be 25.7%.

Example B4

To a 100 mL autoclave were charged 4 g of distilled laurolactam of Example B1 (light transmittance difference (LT. diff)=44.7%), 6 g of toluene and 0.1 g of 5% by weight Pd/C (powder). The system atmosphere was substituted with hydrogen gas, and at a pressure of 0.2 MPa and a temperature of 90° C., the reaction was conducted for 1 hour. At the end of the reaction, the mixture was filtrated through a membrane filter at a temperature of 90° C. The filtrate thus obtained was concentrated (recovery rate: 90%). A light transmittance difference (LT. diff) of laurolactam thus obtained was determined to be 18.4%.

Example B5

To a 100 mL autoclave were charged 4 g of distilled laurolactam of Example B1 (light transmittance difference (LT. diff)=44.7%), 6 g of toluene and 0.1 g of 36.6% by weight Ni/Al$_2$O$_3$ (powder, pre-reduced, 130° C., 0.5 MPa 1 h, toluene 3 g). The system atmosphere was substituted with hydrogen gas, and at a pressure of 0.5 MPa and a temperature of 90° C., the reaction was conducted for 1 hour. At the end of the reaction, the mixture was filtrated through a membrane filter at a temperature of 90° C. The filtrate thus obtained was concentrated (recovery rate: 90%). A light transmittance difference (LT. diff) of laurolactam thus obtained was determined to be 22.9%.

Example B6

To a 100 mL autoclave were charged 4 g of distilled laurolactam of Example B1 (light transmittance difference (LT. diff)=44.7%), 6 g of toluene and 0.1 g of sulfur resistant Ni/Al$_2$O$_3$ (powder, pre-reduced, 130° C., 0.5 Mpa·1 h, toluene 3 g). The system atmosphere was substituted with hydrogen gas, and at a pressure of 0.5 MPa and a temperature of 90° C., the reaction was conducted for 1 hour. At the end of the reaction, the mixture was filtrated through a membrane filter at a temperature of 90° C. The filtrate thus obtained was concentrated (recovery rate: 90%). A light transmittance difference (LT. diff) of laurolactam thus obtained was determined to be 12.6%.

Example B7

To a 300 mL autoclave were charged 130 g of the reaction solution after washing obtained in Reference Example B4 and 13 g of 5% by weight Pt/C (powder) and the system atmosphere was substituted with hydrogen gas. The reaction was conducted at a pressure of 0.5 MPa and a temperature of 90° C. for 2 hours. At the end of the reaction, the mixture was filtrated through a 5C filter paper at a temperature of 90° C., and the filtrate obtained was concentrated (recovery rate: 90%). A light transmittance difference (LT. diff) of laurolactam thus obtained was determined to be 34.5%.

Example B8

To a 300 mL autoclave were charged 130 g of laurolactam obtained in Reference Example B6 and 15 g of 5% by weight Pt/C (powder) and the system atmosphere was substituted with hydrogen gas. The reaction was conducted at a pressure of 0.5 MPa and a temperature of 165° C. for 2 hours. At the end of the reaction, the mixture was diluted with 600 g of toluene and was filtrated through a 5C filter paper at a temperature of 90° C. The filtrate thus obtained was concentrated by rotary evaporation (recovery rate: 90%). A light transmittance difference (LT. diff) of laurolactam thus obtained was determined to be 7.9%.

Example C

In Examples C1 to C7 described below, cyclododecanone oxime was produced using cyclododecanone and then was subjected to Beckmann rearrangement in the presence of a catalyst to give laurolactam, which was purified by hydrogenation or crystallization. Then, for laurolactam thus obtained, a light transmittance difference (LT. diff) was measured and gas chromatography-mass spectrometry was conducted. In Examples C1 to C7 and Reference Examples C1 to C6 described below, a light transmittance difference (LT. diff) was measured as described for Example B.

Gas Chromatography Analysis

Measurement conditions of gas chromatography in Examples C1 to C7 and Reference Example C1 were as follows.

Analytical column: GL Sciences Inc., TC-1 capillary column, column length: 30 m, inner diameter: 0.53 mm, film thickness: 1.5 µm, column temperature: 70 to 300° C., temperature increase rate: 5° C./min.

In Examples C1 to C7 and Reference Examples C1 to C6 described below, a compound produced by [step C1] to [step C5] was used.

Step C1: preparation of Cyclododecanone

Cyclododecanone prepared by a dehydrogenation reaction of a cyclododecanone/cyclododecanol mixture (from Invista) was used as a starting material. A light transmittance difference (LT. diff) of the cyclododecanone was 48%. Gas chromatographic analysis showed an impurity in 230 ppm by weight at a retention time of 23 min, whose analysis by a gas chromatography-mass spectrometer (JEOL Ltd., JMS-GC mate II) showed that a molecular weight was 180. From analysis of a fragment ion, it was identified as cyclododecenone.

Step C2: Production of Cyclododecanone Oxime

Cyclododecanone oxime was produced as described in Reference Example B1, using 7241 g of cyclododecanone prepared by step C1.

Step C3: Drying of Cyclododecanone Oxime

A solution of cyclododecanone oxime in toluene prepared in step C2 was dried as described in Reference Example B2 until a moisture content became 350 ppm. A part of the solution of cyclododecanone oxime in toluene obtained was taken, diluted in toluene and analyzed by gas chromatography under the above conditions, detecting impurities of 51 ppm by weight, 50 ppm by weight and 51 ppm by weight at retention times of 27.1 min, 28.1 min and 28.3 min, respectively. Gas chromatography-mass spectrometry showed that all of these three impurities had a molecular weight of 195, and analysis of fragment ions showed that the sample was a mixture of cyclododecenone oxime isomers.

Step C4: Production of Laurolactam (Thionyl Chloride Catalyst)

Zinc chloride was dissolved in a 50% by weight solution of cyclododecanone oxime in toluene prepared by step C3 such that its amount was 1.0 mol % based on cyclododecanone oxime, and the solution was charged in a multistep reaction apparatus consisting of two 500 mL separable flasks having a jacket equipped with a stirrer (a first rearrangement-reaction tank and a second rearrangement-reaction-tank). Separately, a 10% by weight thionyl chloride-toluene solution was mixed with a cyclododecanone oxime-toluene solution prepared by diluting the above 50% by weight solution of cyclododecanone oxime with toluene to a concentration of 15% by weight to prepare a catalytically active species (this mixing tank is referred to as a pre-preparation reactor), which was then fed to the first rearrangement-reaction tank. The pre-preparation reactor was equipped with a water-cooling jacket for preventing temperature rising due to exotherm, whereby a temperature was controlled to be 35° C. or lower. The amounts of thionyl chloride and cyclododecanone oxime fed to a pre-preparation reactor were 1.5 mol % and 3.75 mol %, respectively, based on the total amount of cyclododecanone oxime fed to the pre-preparation reactor and the first rearrangement-reaction tank, and a residence time in the pre-preparation reactor was 20 min. Furthermore, a temperature of the rearrangement reaction tank was set to 105° C., and a residence time in the rearrangement reaction tanks was set to 25 min in the first and the second rearrangement-reaction tanks in total.

Analysis of the reaction solution in the rearrangement reaction tank by gas chromatography showed that a conversion of cyclododecanone oxime was 100% and a yield of laurolactam was 99.7%. A light transmittance difference (LT. diff) of laurolactam obtained was 65.3%.

Step C5: Post-Treatment and Distillation Purification of a Rearrangement Solution 50 g of water was added to 500 g of the laurolactam/toluene solution prepared by step C4 and the mixture was allowed to stand at 85° C. for 10 min and the phases were separated to obtain a light liquid phase. This operation was further repeated twice. To the light liquid phase obtained was added 64 g of a 1 mol/L aqueous sodium hydroxide solution, and the mixture was stirred at 85° C. for 10 min and then allowed to stand, followed by taking a light liquid phase (referred to as a post-treatment solution). The resulting light liquid phase was evaporated to remove toluene and then distilled (bottom temperature: 190° C., degree of vacuum: 3 to 4 torr, reflux ratio: 1, Sulzer packing: 7 plates) to give laurolactam.

Reference Example C1

Analysis of laurolactam produced in steps C1 to C5 by gas chromatography (under the above conditions) detected impurities at 27.5 min, 29.2 min and 32.6 min in concentrations of 4 ppm by weight, 8 ppm by weight and 21 ppm by weight, respectively. Gas chromatography-mass spectrometry showed that all of these had a molecular weight of 195, and analysis of fragment ions showed that the product was a mixture of dodeceno-12-lactam isomers. A light transmittance difference (LT. diff) of laurolactam obtained was 44.7%.

Reference Example C2

Laurolactam was produced as described in Reference Example C1, substituting step C4' described below for step C4.

Step C4': Production of Laurolactam (Cyanuric Chloride Catalyst)

To the multistep reaction apparatus described in step C4 was fed a solution prepared by dissolving zinc chloride in the 50% by weight cyclododecanone oxime-toluene solution obtained as described in step C3 to 1.0 mol % based on cyclododecanone oxime at such a rate that a total of residence times in two tanks was 25 min. Meanwhile, the cyanuric chloride-toluene solution was fed to the first tank such that the amount of cyanuric chloride was 1.5 mol % based on cyclododecanone oxime. Analysis of the reaction solution in the second tank by gas chromatography showed that a conversion of cyclododecanone oxime was 100% and a yield of laurolactam was 99.7%. A light transmittance difference (LT. diff) of laurolactam obtained was 66.8%.

The laurolactam obtained was purified by the method described in step C5. Analysis of the purified laurolactam by gas chromatography (under the above conditions) detected impurities described in Reference Example C1 (mixture of dodeceno-12-lactam isomers) in 5 ppm by weight, 9 ppm by weight and 20 ppm by weight, respectively. A light transmittance difference (LT. diff) of the laurolactam was 47.0%.

Example C1

Hydrogenation Purification of Cyclododecanone

To 10 kg of cyclododecanone obtained in step C1 was added 10 g of a Pt/C catalyst supporting platinum in 5% by weight (N. E. Chemcat Corp.), and the melt-homogenized slurry was fed to a pressurized-tank flow reactor having a liquid volume of 1 L equipped with a mixing blade at a rate of 1 L/hr (an average residence time: 1 hour) while hydrogen passed through the reactor at 100° C. and 1.1 MPa to conduct hydrogenation. A processed liquid discharged from the pressurized-tank flow reactor was continuously filtrated under pressure to remove the Pt/C catalyst, giving cyclododecanone. Analysis of the cyclododecanone by gas chromatography (under the above conditions) confirmed formation of cyclododecanol in 0.15% by weight and detected no impurities found in step C1, and a light transmittance difference (LT. diff) was 6.5%. Laurolactam was produced as described in Reference Example C1, except the cyclododecanone was used. The purified laurolactam thus obtained did not contain detectable dodeceno-12-lactam found in Reference Example C1, and a light transmittance difference (LT. diff) was 10.1%.

Example C2

Hydrogenation Purification of Cyclododecanone

Laurolactam was produced as described in Example C1, except that a part of the production process for laurolactam was substituted with the process of step C4' as in Reference Example C2. The laurolactam did not contain detectable dodeceno-12-lactam found in Reference Examples C1 and C2, and a light transmittance difference (LT. diff) was 12.1%.

Example C3

Hydrogenation Purification of Cyclododecanone Oxime

A solution of cyclododecanone oxime in toluene was prepared as described in step C2. Using the apparatus described in Example C1, cyclododecanone oxime was hydrogenated under the conditions: the amount of 5% Pt/C: 1% by weight, a hydrogen pressure: 0.2 MPa and an average residence time: 60 min. After drying according to step C3, purified laurolactam was produced as described in steps C4 and C5. Gas chromatographic analysis of the cyclododecanone oxime after drying detected no impurities found in step C3 and dodeceno-12-lactam was not detected in the purified laurolactam. Furthermore, a light transmittance difference (LT. diff) of the purified laurolactam was 15.0%.

Example C4

Crystallization Purification of Cyclododecanone Oxime

Cyclododecanone oxime was produced as described in Reference Example C1 except that a solvent in step C2 was methanol and a reaction temperature was 65° C. At the end of the reaction, an aqueous phase was separated and the reaction solution (cyclododecanone oxime/methanol slurry) was cooled to room temperature, and then cyclododecanone oxime crystals were collected by filtration. A methanolic mother liquid containing cyclododecanone oxime was evaporated under an ambient pressure to remove methanol to be concentrated to about 10 times thereof and then, the concentrate was cooled to room temperature and precipitated cyclododecanone oxime crystals were collected by filtration. The cyclododecanone oxime thus obtained were combined with the crystals precipitated during cooling the reaction solution described above, and rinsed with 500 mL of water and methanol. The crystals were placed in a vacuum dryer and then dried at 70° C. The dried cyclododecanone oxime was dissolved in toluene to prepare a 50% by weight solution of cyclododecanone oxime in toluene, and then, purified laurolactam was produced as described in steps C4 and C5. Concentrations of dodeceno-12-lactam isomers in the purified laurolactam were 1 ppm by weight, 3 ppm by weight and 10 ppm by weight, respectively, and a light transmittance difference (LT. diff) was 21.0%.

Example C5

Hydrogenation Purification of a Post-Treatment Solution

A post-treatment solution was prepared as described in Reference Example C1, except that distillation purification in step C5 was not performed, and was burned in an automatic sample combustion apparatus (Mitsubishi Chemical Corporation, type AQF-100) while a gas generated was absorbed in an aqueous solution of sodium hydroxide, which was then analyzed by ion chromatography (Mitsubishi Chemical Corporation, DIONEX-ICS1000 system). The results indicated 180.4 ppm by weight of chlorine and 56.2 ppm by weight of sulfur. To 200 g of the post-treatment solution was added 10 g of a stabilized nickel catalyst (JGC Catalysts and Chemicals Ltd., F33B:Ni (56% by weight) supported a silica-alumina carrier), and the mixture was treated under a hydrogen pressure of 0.5 MPa at 130° C. for 1.5 hours. The results showed that a light transmittance difference (LT. diff) was 29.7% and chlorine and sulfur were contained in 75.5 ppm and 5.3 ppm, respectively.

After removing the catalyst by filtration, 10 g of an additional stabilized nickel catalyst (JGC Catalysts and Chemicals Ltd., N102F:Ni (62% by weight) supported on a silica-Mg carrier), and the mixture was treated under a hydrogen pressure of 0.5 MPa at 130° C. for 1.5 hours. For the treated solution, a chlorine and a sulfur concentrations were 3.0 ppm by weight and 4.4 ppm, respectively, dodeceno-12-lactam was not detected and a light transmittance difference (LT. diff) was 6.9%.

Example C6

Hydrogenation Purification of Laurolactam

Laurolactam was produced as described in Reference Example C1, and to 120 g of the laurolactam was added 1.2 g of a stabilized nickel catalyst (JGC Catalysts and Chemicals Ltd., N113F:Ni (52% by weight), carrier: diatomaceous earth), and the mixture was treated under a hydrogen pressure of 0.5 MPa at 165° C. for 2 hours. For the laurolactam, chlorine or sulfur was not detected by ion chromatography and dodeceno-12-lactam was not detected. A light transmittance difference (LT. diff) was 4.3%.

Example C7

Hydrogenation Purification of Laurolactam

Laurolactam was hydrogenation-purified as described in Example C6, except that laurolactam was produced as described in Reference Example C2. For the laurolactam, chlorine or sulfur was not detected by ion chromatography and dodeceno-12-lactam was not detected. A light transmittance difference (LT. diff) was 5.1%.

Reference Example C3

Purified laurolactam was produced as described in Reference Example C1 except that a reflux ratio in the distillation conditions in step C5 was increased to 5. The purified laurolactam obtained had a light transmittance difference (LT. diff) of 44.0%. After distillation was repeated under the same conditions, the purified laurolactam had a light transmittance difference (LT. diff) of 35.0%.

Reference Example C4

50 g of charcoal was added to 500 g of the laurolactam/toluene solution prepared in step C4, and the mixture was stirred at 85° C. for 1 hour and then filtrated at the same temperature for removing the activated charcoal. The resulting solution was cooled to room temperature, and precipitated crystals were taken by filtration, washed with 100 g of toluene and dried to give dried crystals. The crystals had a light transmittance difference (LT. diff) of 38.5%.

Reference Example C5

Laurolactam was produced as described in Reference Example C1, except that in the distillation purification of step C5, distillation was conducted after adding 2000 ppm by weight of sodium carbonate powder to the crude laurolactam. The purified laurolactam obtained had a light transmittance difference (LT. diff) of 38.0%.

Reference Example C6

Laurolactam was produced as described in Reference Example C1, except that laurolactam was treated by the first washing with water in the post-treatment of step C4, adding sodium hypochlorite in 1 mol % based on laurolactam. The purified laurolactam obtained had a light transmittance difference (LT. diff) of 43.0%.

Reference Example C7

Laurolactam was produced as described in Reference Example C1, except that laurolactam was treated by the first washing with water in the post-treatment of step C4, adding an ion-exchange resin (Organo Corporation, Amberlyst 15DRY) in 5 mol % based on laurolactam. The purified laurolactam obtained had a light transmittance difference (LT. diff) of 44.0%.

Example D

In Examples D1 to D4 below, cyclododecanone oxime was produced using cyclododecanone purified by recrystallization, and a laurolactam solution and so on were analyzed for impurities.

Example D1

Production of Cyclododecanone

Cyclododecanone was produced as described in Japanese laid-open patent publication No. 2007-506695. Specifically, at first, butadiene was trimerized using titanium tetrachloride and ethylaluminum sesquichloride as catalysts, to produce cyclododecatriene. Next, cyclododecatriene was oxidized by nitrous oxide to give cyclododecadienone, and a remaining carbon-carbon double bond was hydrogenated over a palladium catalyst to produce crude cyclododecanone. The crude cyclododecanone obtained was purified by distillation to give cyclododecanone as a starting material.

Analysis of Impurities in Cyclododecanone

The cyclododecanone obtained was analyzed by gas chromatography (Column: GL Sciences Inc., CP-SIL19CB, 50 m capillary column, column temperature: 70° C. to 300° C. at a rate of rising temperature of 5° C./min), and then impurities were detected at retention times of 24.68 min, 24.73 min, 24.87 min and 25.12 min with weight concentrations of 165 ppm by weight, 107 ppm by weight, 147 ppm by weight and 145 ppm by weight, respectively. Gas chromatography-mass spectrometry (JEOL Ltd., JMS-GC mate II) showed that all of these had a molecular weight of 178. To 10 g of the cyclododecanone was added 0.5 g of platinum/carbon containing 5% by weight of platinum (N. E. Chemcat Corp.), and the mixture was hydrogenated under a hydrogen pressure of 1 MPa at 110° C. for 1 hour. Gas chromatography analysis showed that concentrations of the impurities at a retention times of 24.68 min, 24.73 min and 24.87 min were unchanged while the impurity at 25.12 min disappeared. It, therefore, implies that the impurities at retention times of 24.68 min, 24.73 min and 24.87 min are dodecanone having a tricyclic ring structure and the impurity at 25.12 min is dodecenone having a dicyclic ring structure or cyclododecadienone.

Purification of Cyclododecanone by Recrystallization

To 100 parts by weight of cyclododecanone was added 8 parts by weight of n-heptane, and the mixture was heated to 60° C. for dissolution, then cooled to 25° C., and crystals of cyclododecanone was taken by filtration. The crystals were washed with 3 parts by weight of n-heptane and dried to give crystals of purified cyclododecanone. A one-pass yield in the crystallization was 76.6% and gas chromatography analysis showed that impurities at retention times of 24.68 min, 24.73 min and 24.87 min were reduced to 4 ppm by weight, 4 ppm by weight and 6 ppm by weight, respectively while the impurity at 25.12 min was not detected.

Production of Laurolactam

Laurolactam was produced as described in Japanese laid-open patent publication No. 1993-4964. At first, a separately prepared cyclohexanone was fed to a first oxime-forming tank, and mixed, with stirring, with a second oxime-forming tank heavy liquid consisting of hydroxylamine sulfate and an aqueous solution of ammonium sulfate. To the mixture was added dropwise aqueous ammonia while pH was adjusted, to produce cyclohexanone oxime. The resulting cyclohexanone oxime melt was fed to the second oxime-forming tank. To the second oxime-forming was fed the aqueous solution of cyclododecanone and hydroxylamine sulfate prepared as described above, and as in the first oxime-forming tank, aqueous ammonia was added dropwise with stirring to produce cyclododecanone oxime. The amount of the aqueous solution of hydroxylamine sulfate fed to the second oxime-forming tank was equimolar to the total of cyclohexanone and cyclododecanone. The light liquid phase discharged from the second oxime-forming tank was a melt consisting of cyclohexanone oxime and cyclododecanone oxime, which was supplied to a rearrangement step. In the rearrangement step, cyclohexanone oxime and cyclododecanone oxime were rearranged by concentrated sulfuric acid and oleum. At the end of the rearrangement, aqueous ammonia was added to the rearrangement solution for neutralize sulfuric acid, to liberate caprolactam and laurolactam, which was then extracted with toluene. Water was added to the resulting solution of caprolactam and laurolactam in toluene for extracting caprolactam into the aqueous phase, separating them. Each of the aqueous solution of caprolactam and the solution of laurolactam in toluene thus obtained was evaporated to give a crude lactam, which was further purified by distillation to give a product lactam.

Distillation purification of laurolactam was conducted by continuous distillation using three columns. The first column was for a low-boiling point component removing column, where a low-boiling component was distilled from the top of the column while bottoms were fed to the second column. In the second column, a product laurolactam was distilled from the top of the column while bottoms containing high-boiling impurities were fed to the third column. The distillation fraction from the top of the third column was recycled to the second column while from the bottom of the column, laurolactam containing high-boiling impurities was discharged. The discharge amount from the tower bottom was 0.01% by weight based on the obtained amount of the product laurolactam.

Analysis of Impurities in Laurolactam

To 100 g of the above crude laurolactam or the product laurolactam was added 100 g of methanol and the mixture was heated at 65° C. for dissolving. The solution of laurolactam in methanol was cooled to 20° C., and the precipitated laurolactam was taken by filtration. The filtrate was evaporated to dryness. The resulting solid was heated at 65° C. followed by addition of a small amount of methanol, and the mixture was heated at 65° C. for dissolving and then cooled to 20° C., and the precipitated laurolactam was taken by filtration. The filtrate obtained was increased to 5.0 g. Analysis of the filtrate by gas chromatography (column: GL Sciences Inc., TC-1, 30 m capillary column, temperature: programmed from 70° C. to 300° C. at a rate of rising temperature of 5° C./min) detected impurities at retention times of 31.3 min and 31.7 min, and their contents were 3.1 ppm by weight and 6.0 ppm by weight in the crude laurolactam and 0.5 ppm by weight and 0.9 ppm by weight in the distillation purified laurolactam as a product. Analysis by gas chromatography-mass spectrometry (JEOL Ltd., JMS-GC mate II) showed that these impurities had a molecular weight of 193. To 3 g of the filtrate was added 0.15 g of platinum/carbon containing 5% by weight of platinum (N. E. Chemcat Corp.), and the mixture was hydrogenated under a hydrogen pressure of 1 MPa at 110° C. for 1 hour, and then gas chromatography analysis showed that concentrations of both of the impurities were unchanged. These impurities were, therefore, supposed to be dodecanolactam having a tricyclic ring structure.

Reference Example D1

A product laurolactam was prepared as described in Example D1, except that purification of cyclododecanone was not performed and in distillation purification of laurolactam, a discharge rate from the column bottom was 0.12% by weight based on the amount of the product laurolactam obtained. In the crude laurolactam, impurities were detected at retention times of 30.9 min, 31.3 min, 31.6 min, 31.7 min, 32.0 min, 32.5 min and 32.7 min, whose concentrations were 35 ppm by weight, 96 ppm by weight, 35 ppm by weight, 163 ppm by weight, 15 ppm by weight and 32 ppm by weight, respectively, based on the crude laurolactam. These impurities were detected in the product laurolactam in 7 ppm by weight, 16 ppm by weight, 7 ppm by weight, 32 ppm by weight, 2 ppm by weight and 4 ppm by weight, respectively. Gas chromatography-mass spectrometry showed that all of the impurities had a molecular weight of 193. After hydrogenation of the product laurolactam, concentrations of the impurities at retention times of 30.9 min, 31.3 min, 31.6 min, 31.7 min, 32.0 min and 32.5 min were unchanged after the process while the impurity at 32.7 min disappeared and new impurities were detected at 32.1 min and 32.6 min, whose concentrations were 1 ppm by weight and 3 ppm by weight, respectively, based on the product laurolactam. The new impurities had a molecular weight of 195. The above results imply that the impurities at 30.9 min, 31.3 min, 31.6 min, 31.7 min, 32.0 min and 32.5 min are dodecanolactam having a tricyclic ring structure while the impurity at 32.7 min is dodecenolactam having a dicyclic ring structure.

Example D2

Laurolactam was prepared as described in Example D1, except that a recrystallization solvent for cyclododecanone was methanol. A one pass yield in the crystallization purification of cyclododecanone was 87.6%, and the impurities at retention times of 24.68 min and 24.73 min were contained in 4 ppm by weight and 6 ppm by weight, respectively while the impurity at 24.87 min or 25.12 min was not detected. In the product laurolactam, the impurity at 31.3 min was contained in 0.5 ppm by weight while the impurity at 31.7 min was not detected.

Example D3

Laurolactam was prepared as described in Example D1, except that a recrystallization solvent for cyclododecanone was toluene. A one pass yield in the recrystallization purification of cyclododecanone was 35.8%, and the impurities at retention times of 24.68 min and 24.87 min were contained in 4 ppm by weight and 9 ppm by weight, respectively while the impurity at 24.73 min or 25.12 min was not detected. In the product laurolactam, the impurities at 31.3 min and 31.7 min were contained in 0.5 ppm by weight and 1.1 ppm by weight, respectively.

Example D4

Laurolactam was produced as described in Example D1, except that production of cyclododecanone oxime and the step of its rearrangement reaction were as described below.

To a pillow type first oxime-forming reactor with a liquid-phase volume of 30 L whose inside was divided into four chambers, each of which was equipped with a mixing blade, were fed a 15% by weight aqueous solution of hydroxylamine sulfate (Wako Pure Chemical Industries, Ltd.) at 1.5 kg/h and an oil phase supplied from a second oxime-forming reactor. A reaction temperature was set to 95° C., and 25% by weight of aqueous ammonia was fed to each chamber at 32 g/h to initiate an oxime-forming reaction to give an oil phase consisting of cyclododecanone oxime and toluene.

The aqueous phase was fed to the second oxime-forming reactor. The second oxime-forming reactor was a 15 L pillow type reactor whose inside was divided into four chambers. The aqueous phase of the oxime-forming reaction solution and a 25% by weight cyclododecanone solution prepared by dissolving the purified cyclododecanone obtained in Example D1 in toluene at 2 kg/h (in an equimolar amount to hydroxylamine sulfate fed to the first reactor) were fed to the reactor, and a reaction temperature was set to 95° C. and a 25% by weight aqueous ammonia was fed to each chamber at 16 g/h to initiate an oxime-forming reaction. The reaction solution thus obtained was phase-separated and the oil phase was fed to the first oxime-forming reactor.

To a 20 L evaporator was placed 10 kg of the oil phase obtained in the first oxime-forming reactor, and toluene was removed by evaporation to give 5.26 kg of a solution of cyclododecanone oxime in toluene. A content of cyclododecanone oxime was quantitatively analyzed by gas chromatography, and a content of cyclododecanone oxime was 50% by weight.

To a glass mixing unit (internal volume: 2.5 ml) equipped with a jacket were fed a 10% by weight solution of thionyl chloride (rearrangement catalyst) in toluene at 27.7 g/h and a 20% by weight solution of cyclododecanone oxime/toluene prepared by diluting the 50% by weight solution of cyclododecanone/toluene with toluene at 57.5 g/h, and the mixture was mixed with a stirring bar while an internal temperature of the mixing unit was controlled at 25° C. by a jacket cooling medium. A molar ratio of cyclododecanone oxime to thionyl chloride was 2.5. The mixed solution was fed to a glass pre-preparation reactor having an inner volume of 48 mL equipped with a jacket through an inlet tube. Here a residence time from the mixing unit to the pre-preparation reactor was 1.5 min and a residence time in the pre-preparation reactor was 29 min. An internal temperature of a degassing tank was controlled to 35° C. by a jacket cooling medium while the mixture was degassed by nitrogen (40 mL/min) with stirring by a stirrer for pre-preparation, and an overflow liquid flowed down to the rearrangement reaction tank.

Meanwhile, a solution prepared by adding zinc chloride to a 50% by weight solution of cyclododecanone oxime/toluene in 1 mol % based on the cyclododecane oxime was fed to the rearrangement reaction tank at 613 g/h. The rearrangement reaction tank consisted of two CSTRs (Continuous Stirred Tank Flow Reactor) having an internal volume of 163 mL, and a heat-medium temperature was adjusted such that a liquid temperature became to be 105° C. A reaction time (the total of average residence-times in CSTR 1 and 2) was 0.4 hours, and under the same conditions, a continuous reaction was continuously conducted for 9.5 hours. As a result, a molar production ratio of a catalytically active species in the pre-preparation liquid introduced from the degassing tank into the rearrangement reaction reactor based on thionyl chloride added in the pre-preparation was 96.2%, (the catalytically active species is cyclododecanone O-azacyclotridecen-2-yl oxime hydrochloride represented by formula (6) (this compound denotes the compound represented by formula (6), or a stereoisomer other than the compound represented by formula (6), or a mixture of a combination of stereoisomers containing the compound represented by formula (6)). In the rearrangement reaction using this pre-preparation liquid, a conversion of cyclododecanone oxime was 99.97% and a yield of laurolactam was 99.8%.

The rearrangement reaction solution obtained was washed with water and then with a 4% by weight aqueous solution of sodium hydroxide to remove the residual catalyst and so on, and then, toluene was removed by evaporation to give a crude laurolactam. Furthermore, as described in Example D1, distillation purification was conducted to give a product laurolactam. In the crude laurolactam and the product laurolactam after distillation purification, the impurities at 31.3 min and 31.7 min were contained in 3.5 ppm by weight and 5.5 ppm by weight, and 0.6 ppm by weight and 0.8 ppm by weight, respectively.

Example D5

A crude cyclododecanone was produced as described in Japanese laid-open patent publication No. 2000-256340, No. 2000-026441, No. 2001-302650 and No. 2001-226311. Specifically, 1,5,9-cyclododecatriene was blended with hydrogen peroxide water, and phosphotungstic acid and trioctylmethylammonium chloride as catalysts were added to initiate oxidation, giving 1,2-epoxy-5,9-cyclododecadiene. After recovering unreacted 1,5,9-cyclododecatriene by distillation, 1,2-epoxy-5,9-cyclododecadiene was purified by distillation. 1,2-Epoxy-5,9-cyclododecadiene thus obtained was hydrogenated over platinum/carbon as a catalyst, to hydrogenate a double bond. To the epoxycyclododecane thus obtained was added lithium iodide as a catalyst, and the mixture was heated to 230° C. for isomerization to give cyclododecanone. Purification of cyclododecanone and production of laurolactam were conducted as described in Example D1, and impurities were analyzed. In cyclododecanone after purification, the impurities at 24.68 min, 24.73 min and 24.87 min were contained in 2.4 ppm by weight, 2.1 ppm by weight and 4.1 ppm by weight, respectively, while the impurity at 25.12 min was not detected. In a crude laurolactam and a product laurolactam, the impurities at 31.3 min and 31.7 min were contained in 2.1 ppm by weight and 4.0 ppm by weight, and 0.3 ppm by weight and 0.6 ppm by weight, respectively.

What is claimed is:

1. A process for producing a lactam, comprising:
reacting a cyclic ketone and hydroxylamine to give an oxime; and
conducting Beckmann rearrangement of the oxime using a Beckmann rearrangement catalyst to give a lactam,
wherein the rearrangement catalyst is
at least one selected from the group consisting of 4-chloro-3,5-dinitrobenzonitrile, picryl chloride, 2-chloro-3,5-dinitropyridine, trichlorotriazine, thionyl chloride, phosphorous trichloride and phosphorous pentachloride; and
purifying one or more of compounds selected from the group consisting of a cyclic ketone, an oxime and a lactam by hydrogenation and/or crystallization,
wherein the lactam is caprolactam and/or laurolactam, the cyclic ketone is cyclohexanone and/or cyclododecanone, and the oxime is cyclohexanone oxime and/or cyclododecanone oxime.

2. The process for producing the lactam according to claim 1, wherein the cyclic ketone is purified by hydrogenation.

3. The process for producing the lactam according to claim 1, wherein the oxime is purified by crystallization.

4. The process for producing the lactam according to claim 1, wherein the oxime is purified by hydrogenation.

5. The process according to claim 1, wherein the lactam prepared by Beckmann rearrangement of the oxime is purified by hydrogenation.

* * * * *

UNITED STATES PATENT AND TRADEMARK OFFICE
CERTIFICATE OF CORRECTION

PATENT NO. : 8,962,826 B2
APPLICATION NO. : 14/141916
DATED : February 24, 2015
INVENTOR(S) : Junichi Kugimoto et al.

It is certified that error appears in the above-identified patent and that said Letters Patent is hereby corrected as shown below:

In the specification

Col. 14, line 31, "shiff base" should be --schiff base--.

Col. 16, line 33, "9, or" should be --9, 10 or--.

Col. 17, line 67, "N,N-" should be --N,N'- --.

Col. 18, line 1, "N-hydroxyglutalimide," should be --N-hydroxyglutarimide,--.

Col. 23, line 45, "pyrrol" should be --pyrrole--.

Col. 26, line 54, "shot" should be --short--.

Col. 26, line 66, "prepreparation" should be --pre-preparation--.

Col. 27, line 40, "Broensted" should be --Bronsted--.

Col. 27, line 57, "Broensted" should be --Bronsted--.

Col. 37, line 52, "MPa 1" should be --MPa. 1--.

Signed and Sealed this
Fifth Day of January, 2016

Michelle K. Lee
*Director of the United States Patent and Trademark Office*